United States Patent
Verker et al.

(10) Patent No.: US 10,507,088 B2
(45) Date of Patent: *Dec. 17, 2019

(54) IMAGING APPARATUS WITH SIMPLIFIED OPTICAL DESIGN

(71) Applicant: Align Technology, Inc., San Jose, CA (US)

(72) Inventors: Tal Verker, Ofra (IL); Adi Levin, Nes Tziona (IL); Ofer Saphier, Rechovot (IL); Maayan Moshe, Ra'anana (IL)

(73) Assignee: Align Technology, Inc., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/286,437

(22) Filed: Feb. 26, 2019

(65) Prior Publication Data

US 2019/0192263 A1    Jun. 27, 2019

Related U.S. Application Data

(60) Continuation of application No. 15/610,515, filed on May 31, 2017, now Pat. No. 10,327,872, which is a
(Continued)

(51) Int. Cl.
*G02B 23/24* (2006.01)
*G02B 21/00* (2006.01)
(Continued)

(52) U.S. Cl.
CPC ............ *A61C 9/0066* (2013.01); *G01B 11/24* (2013.01); *G02B 21/006* (2013.01);
(Continued)

(58) Field of Classification Search
CPC .... A61C 9/0066; G01B 11/24; G02B 21/006; G02B 23/2446; G02B 23/2461; G02B 23/26; G02B 27/0025
(Continued)

(56) References Cited

U.S. PATENT DOCUMENTS 2,171,695 A    9/1939 Harper
2,467,432 A    4/1949 Kesling
(Continued)

FOREIGN PATENT DOCUMENTS

AU    3031677 A    5/1979
AU    3031677 B    7/1981
(Continued)

OTHER PUBLICATIONS

Kleeman et al., "The Speed Positioner", J. Clin. Orthod.; 30(12); pp. 673-680; Dec. 1996.
(Continued)

*Primary Examiner* — Isiaka O Akanbi
(74) *Attorney, Agent, or Firm* — Lowenstein Sandler LLP

(57) ABSTRACT

Embodiments are directed to an imaging apparatus, which in an embodiment includes a light source to provide light, optics, a translation mechanism and a detector. The optics include focusing optics to perform focusing of the light onto a non-flat focal surface and to direct the light toward a three dimensional object. The translation mechanism adjusts a location of at least one lens of the focusing optics to displace the non-flat focal surface. The detector measures intensities of returning light that is reflected off of the three dimensional object, wherein the intensities of the returning light are measured for a plurality of locations of the at least one lens for determination of positions of a plurality of points of the three dimensional object. Detected positions of one or more of the plurality of points are adjusted to compensate for the non-flat focal surface.

30 Claims, 13 Drawing Sheets

Related U.S. Application Data division of application No. 14/825,173, filed on Aug. 13, 2015, now Pat. No. 9,675,430.

(60) Provisional application No. 62/037,778, filed on Aug. 15, 2014.

(51) Int. Cl.
  *A61C 9/00* (2006.01)
  *G01B 11/24* (2006.01)
  *G02B 27/00* (2006.01)
  *G02B 23/26* (2006.01)

(52) U.S. Cl.
  CPC ..... *G02B 23/2446* (2013.01); *G02B 23/2461* (2013.01); *G02B 23/26* (2013.01); *G02B 27/0025* (2013.01)

(58) Field of Classification Search
  USPC .......................................... 356/601, 445, 603
  See application file for complete search history.

(56) References Cited

U.S. PATENT DOCUMENTS

| | | |
|---|---|---|
| 2,531,222 A | 11/1950 | Kesling |
| 3,379,193 A | 4/1968 | Monsghan |
| 3,385,291 A | 5/1968 | Martin |
| 3,407,500 A | 10/1968 | Kesling |
| 3,478,742 A | 11/1969 | Bohlmann |
| 3,496,936 A | 2/1970 | Gores |
| 3,533,163 A | 10/1970 | Kirschenbaum |
| 3,556,093 A | 1/1971 | Quick |
| 3,600,808 A | 8/1971 | Reeve |
| 3,660,900 A | 5/1972 | Andrews |
| 3,683,502 A | 8/1972 | Wallshein |
| 3,738,005 A | 6/1973 | Cohen et al. |
| 3,860,803 A | 1/1975 | Levine |
| 3,885,310 A | 5/1975 | Northcutt |
| 3,916,526 A | 11/1975 | Schudy |
| 3,922,786 A | 12/1975 | Lavin |
| 3,950,851 A | 4/1976 | Bergersen |
| 3,983,628 A | 10/1976 | Acevedo |
| 4,014,096 A | 3/1977 | Dellinger |
| 4,195,046 A | 3/1980 | Kesling |
| 4,253,828 A | 3/1981 | Coles et al. |
| 4,255,138 A | 3/1981 | Frohn |
| 4,324,546 A | 4/1982 | Heitlinger et al. |
| 4,324,547 A | 4/1982 | Arcan et al. |
| 4,348,177 A | 9/1982 | Kurz |
| 4,419,992 A | 12/1983 | Chorbajian |
| 4,433,956 A | 2/1984 | Witzig |
| 4,478,580 A | 10/1984 | Barrut |
| 4,500,294 A | 2/1985 | Lewis |
| 4,505,673 A | 3/1985 | Yoshii |
| 4,519,386 A | 5/1985 | Sullivan |
| 4,526,540 A | 7/1985 | Dellinger |
| 4,575,330 A | 3/1986 | Hull |
| 4,575,805 A | 3/1986 | Moermann et al. |
| 4,591,341 A | 5/1986 | Andrews |
| 4,609,349 A | 9/1986 | Cain |
| 4,611,288 A | 9/1986 | Duret et al. |
| 4,656,860 A | 4/1987 | Orthuber et al. |
| 4,663,720 A | 5/1987 | Duret et al. |
| 4,664,626 A | 5/1987 | Kesling |
| 4,676,747 A | 6/1987 | Kesling |
| 4,755,139 A | 7/1988 | Abbatte et al. |
| 4,757,824 A | 7/1988 | Chaumet |
| 4,763,791 A | 8/1988 | Halverson et al. |
| 4,764,111 A | 8/1988 | Knierim |
| 4,793,803 A | 12/1988 | Martz |
| 4,798,534 A | 1/1989 | Breads |
| 4,836,778 A | 6/1989 | Baumrind et al. |
| 4,837,732 A | 6/1989 | Brandestini et al. |
| 4,850,864 A | 7/1989 | Diamond |
| 4,850,865 A | 7/1989 | Napolitano |
| 4,856,991 A | 8/1989 | Breads et al. |
| 4,877,398 A | 10/1989 | Kesling |
| 4,880,380 A | 10/1989 | Martz |
| 4,886,451 A | 12/1989 | Cetlin |
| 4,889,238 A | 12/1989 | Batchelor |
| 4,890,608 A | 1/1990 | Steer |
| 4,935,635 A | 6/1990 | O'Harra |
| 4,936,862 A | 6/1990 | Walker et al. |
| 4,937,928 A | 7/1990 | van der Zel |
| 4,941,826 A | 7/1990 | Loran et al. |
| 4,952,928 A | 8/1990 | Carroll et al. |
| 4,964,770 A | 10/1990 | Steinbichler et al. |
| 4,975,052 A | 12/1990 | Spencer et al. |
| 4,983,334 A | 1/1991 | Adell |
| 4,997,369 A | 3/1991 | Shafir |
| 5,002,485 A | 3/1991 | Aagesen |
| 5,011,405 A | 4/1991 | Lemchen |
| 5,017,133 A | 5/1991 | Miura |
| 5,027,281 A | 6/1991 | Rekow et al. |
| 5,035,613 A | 6/1991 | Breads et al. |
| 5,037,295 A | 8/1991 | Bergersen |
| 5,055,039 A | 10/1991 | Abbatte et al. |
| 5,100,316 A | 3/1992 | Wildman |
| 5,103,838 A | 4/1992 | Yousif |
| 5,121,333 A | 6/1992 | Riley et al. |
| 5,123,425 A | 6/1992 | Shannon, Jr. et al. |
| 5,128,870 A | 7/1992 | Erdman et al. |
| 5,130,064 A | 7/1992 | Smalley et al. |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,176,517 A | 1/1993 | Truax |
| 5,204,670 A | 4/1993 | Stinton |
| 5,242,304 A | 4/1993 | Truax et al. |
| 5,245,592 A | 9/1993 | Kuemmel et al. |
| 5,273,429 A | 12/1993 | Rekow et al. |
| 5,278,756 A | 1/1994 | Lemchen et al. |
| 5,306,144 A | 4/1994 | Hibst et al. |
| 5,328,362 A | 7/1994 | Watson et al. |
| 5,335,657 A | 8/1994 | Terry, Jr. et al. |
| 5,338,198 A | 8/1994 | Wu et al. |
| 5,340,309 A | 8/1994 | Robertson |
| 5,342,202 A | 8/1994 | Deshayes |
| 5,368,478 A | 11/1994 | Andreiko et al. |
| 5,372,502 A | 12/1994 | Massen et al. |
| 5,382,164 A | 1/1995 | Stern |
| 5,395,238 A | 3/1995 | Andreiko et al. |
| 5,431,562 A | 7/1995 | Andreiko et al. |
| 5,440,326 A | 8/1995 | Quinn |
| 5,440,496 A | 8/1995 | Andersson et al. |
| 5,447,432 A | 9/1995 | Andreiko et al. |
| 5,452,219 A | 9/1995 | Dehoff et al. |
| 5,454,717 A | 9/1995 | Andreiko et al. |
| 5,456,600 A | 10/1995 | Andreiko et al. |
| 5,474,448 A | 12/1995 | Andreiko et al. |
| RE35,169 E | 3/1996 | Lemchen et al. |
| 5,499,633 A | 3/1996 | Fenton |
| 5,528,735 A | 6/1996 | Strasnick et al. |
| 5,533,895 A | 7/1996 | Andreiko et al. |
| 5,542,842 A | 8/1996 | Andreiko et al. |
| 5,543,780 A | 8/1996 | McAuley et al. |
| 5,549,476 A | 8/1996 | Stern |
| 5,562,448 A | 10/1996 | Mushabac |
| 5,570,182 A | 10/1996 | Nathel et al. |
| 5,587,912 A | 12/1996 | Andersson et al. |
| 5,605,459 A | 2/1997 | Kuroda et al. |
| 5,607,305 A | 3/1997 | Andersson et al. |
| 5,614,075 A | 3/1997 | Andre, Sr. |
| 5,621,648 A | 4/1997 | Crump |
| 5,626,537 A | 5/1997 | Danyo et al. |
| 5,645,420 A | 7/1997 | Bergersen |
| 5,645,421 A | 7/1997 | Slootsky |
| 5,651,671 A | 7/1997 | Seay et al. |
| 5,655,653 A | 8/1997 | Chester |
| 5,659,420 A | 8/1997 | Wakai et al. |
| 5,683,243 A | 11/1997 | Andreiko et al. |
| 5,683,244 A | 11/1997 | Truax |
| 5,691,539 A | 11/1997 | Pfeiffer |

(56) References Cited

U.S. PATENT DOCUMENTS

| | | |
|---|---|---|
| 5,692,894 A | 12/1997 | Schwartz et al. |
| 5,725,376 A | 3/1998 | Poirier |
| 5,725,378 A | 3/1998 | Wang |
| 5,737,084 A | 4/1998 | Ishihara |
| 5,740,267 A | 4/1998 | Echerer et al. |
| 5,742,700 A | 4/1998 | Yoon et al. |
| 5,769,631 A | 6/1998 | Williams |
| 5,774,425 A | 6/1998 | Ivanov et al. |
| 5,790,242 A | 8/1998 | Stern et al. |
| 5,799,100 A | 8/1998 | Clarke et al. |
| 5,800,174 A | 9/1998 | Andersson |
| 5,816,800 A | 10/1998 | Brehm et al. |
| 5,818,587 A | 10/1998 | Devaraj et al. |
| 5,823,778 A | 10/1998 | Schmitt et al. |
| 5,848,115 A | 12/1998 | Little et al. |
| 5,857,853 A | 1/1999 | van Nifterick et al. |
| 5,866,058 A | 2/1999 | Batchelder et al. |
| 5,879,158 A | 3/1999 | Doyle et al. |
| 5,880,961 A | 3/1999 | Crump |
| 5,880,962 A | 3/1999 | Andersson et al. |
| 5,904,479 A | 5/1999 | Staples |
| 5,934,288 A | 8/1999 | Avila et al. |
| 5,957,686 A | 9/1999 | Anthony |
| 5,964,587 A | 10/1999 | Sato |
| 5,971,754 A | 10/1999 | Sondhi et al. |
| 5,975,893 A | 11/1999 | Chishti et al. |
| 5,980,246 A | 11/1999 | Ramsay et al. |
| 5,989,023 A | 11/1999 | Summer et al. |
| 6,044,309 A | 3/2000 | Honda |
| 6,049,743 A | 4/2000 | Baba |
| 6,053,731 A | 4/2000 | Heckenberger |
| 6,068,482 A | 5/2000 | Snow |
| 6,099,303 A | 8/2000 | Gibbs et al. |
| 6,099,314 A | 8/2000 | Kopelman et al. |
| 6,123,544 A | 9/2000 | Cleary |
| 6,152,731 A | 11/2000 | Jordan et al. |
| 6,154,676 A | 11/2000 | Levine |
| 6,183,248 B1 | 2/2001 | Chishti et al. |
| 6,186,780 B1 | 2/2001 | Hibst et al. |
| 6,190,165 B1 | 2/2001 | Andreiko et al. |
| 6,200,133 B1 | 3/2001 | Kittelsen |
| 6,201,880 B1 | 3/2001 | Elbaum et al. |
| 6,212,435 B1 | 4/2001 | Lattner et al. |
| 6,217,334 B1 | 4/2001 | Hultgren |
| 6,231,338 B1 | 5/2001 | de Josselin de Jong et al. |
| 6,239,705 B1 | 5/2001 | Glen |
| 6,243,601 B1 | 6/2001 | Wist |
| 6,263,234 B1 | 7/2001 | Engelhardt et al. |
| 6,299,438 B1 | 10/2001 | Sahagian et al. |
| 6,309,215 B1 | 10/2001 | Phan et al. |
| 6,315,553 B1 | 11/2001 | Sachdeva et al. |
| 6,328,745 B1 | 12/2001 | Ascherman |
| 6,334,073 B1 | 12/2001 | Levine |
| 6,350,120 B1 | 2/2002 | Sachdeva et al. |
| 6,364,660 B1 | 4/2002 | Durbin et al. |
| 6,382,975 B1 | 5/2002 | Poirier |
| 6,402,510 B1 | 6/2002 | Williams |
| 6,402,707 B1 | 6/2002 | Ernst |
| 6,405,729 B1 | 6/2002 | Thornton |
| 6,436,058 B1 | 8/2002 | Krahner et al. |
| 6,450,807 B1 | 9/2002 | Chishti et al. |
| 6,482,298 B1 | 11/2002 | Bhatnagar |
| 6,499,995 B1 | 12/2002 | Schwartz |
| 6,515,593 B1 | 2/2003 | Stark et al. |
| 6,516,805 B1 | 2/2003 | Thornton |
| 6,520,772 B2 | 2/2003 | Williams |
| 6,524,101 B1 | 2/2003 | Phan et al. |
| 6,540,707 B1 | 4/2003 | Stark et al. |
| 6,572,372 B1 | 6/2003 | Phan et al. |
| 6,573,998 B2 | 6/2003 | Cohen-Sabban |
| 6,594,539 B1 | 7/2003 | Geng |
| 6,597,934 B1 | 7/2003 | de Jong et al. |
| 6,602,070 B2 | 8/2003 | Miller et al. |
| 6,611,783 B2 | 8/2003 | Kelly, Jr. et al. |
| 6,613,001 B1 | 9/2003 | Dworkin |
| 6,616,579 B1 | 9/2003 | Reinbold et al. |
| 6,623,698 B2 | 9/2003 | Kuo |
| 6,624,752 B2 | 9/2003 | Klitsgaard et al. |
| 6,626,180 B1 | 9/2003 | Kittelsen et al. |
| 6,640,128 B2 | 10/2003 | Vilsmeier et al. |
| 6,697,164 B1 | 2/2004 | Babayoff et al. |
| 6,702,765 B2 | 3/2004 | Robbins et al. |
| 6,702,804 B1 | 3/2004 | Ritter et al. |
| 6,705,863 B2 | 3/2004 | Phan et al. |
| 6,830,450 B2 | 12/2004 | Knopp et al. |
| 6,885,464 B1 | 4/2005 | Pfeiffer et al. |
| 6,890,285 B2 | 5/2005 | Rahman et al. |
| 7,036,514 B2 | 5/2006 | Heck |
| 7,092,107 B2 | 8/2006 | Babayoff et al. |
| 7,106,233 B2 | 9/2006 | Schroeder et al. |
| 7,112,065 B2 | 9/2006 | Kopelman et al. |
| 7,121,825 B2 | 10/2006 | Chishti et al. |
| 7,138,640 B1 | 11/2006 | Delgado et al. |
| 7,142,312 B2 | 11/2006 | Quadling et al. |
| 7,166,063 B2 | 1/2007 | Rahman et al. |
| 7,184,150 B2 | 2/2007 | Quadling et al. |
| 7,192,273 B2 | 3/2007 | McSurdy, Jr. |
| 7,220,124 B2 | 5/2007 | Taub et al. |
| 7,286,954 B2 | 10/2007 | Kopelman et al. |
| 7,292,759 B2 | 11/2007 | Boutoussov et al. |
| 7,302,842 B2 | 12/2007 | Biester et al. |
| 7,338,327 B2 | 3/2008 | Sticker et al. |
| D565,509 S | 4/2008 | Fechner et al. |
| 7,351,116 B2 | 4/2008 | Dold |
| 7,357,637 B2 | 4/2008 | Liechtung |
| 7,450,231 B2 | 11/2008 | Johs et al. |
| 7,458,810 B2 | 12/2008 | Bergersen |
| 7,460,230 B2 | 12/2008 | Johs et al. |
| 7,462,076 B2 | 12/2008 | Walter et al. |
| 7,463,929 B2 | 12/2008 | Simmons |
| 7,500,851 B2 | 3/2009 | Williams |
| D594,413 S | 6/2009 | Palka et al. |
| 7,544,103 B2 | 6/2009 | Walter et al. |
| 7,553,157 B2 | 6/2009 | Abolfathi et al. |
| 7,561,273 B2 | 7/2009 | Stautmeister et al. |
| 7,577,284 B2 | 8/2009 | Wong et al. |
| 7,596,253 B2 | 9/2009 | Wong et al. |
| 7,597,594 B2 | 10/2009 | Stadler et al. |
| 7,609,875 B2 | 10/2009 | Liu et al. |
| D603,796 S | 11/2009 | Sticker et al. |
| 7,616,319 B1 | 11/2009 | Woollam et al. |
| 7,626,705 B2 | 12/2009 | Altendorf |
| 7,632,216 B2 | 12/2009 | Rahman et al. |
| 7,633,625 B1 | 12/2009 | Woollam et al. |
| 7,637,262 B2 | 12/2009 | Bailey |
| 7,668,355 B2 | 2/2010 | Wong et al. |
| 7,670,179 B2 | 3/2010 | Muller |
| 7,695,327 B2 | 4/2010 | Bauerle et al. |
| 7,698,068 B2 | 4/2010 | Babayoff |
| 7,724,378 B2 | 5/2010 | Babayoff |
| D618,619 S | 6/2010 | Walter |
| 7,731,508 B2 | 6/2010 | Borst |
| 7,735,217 B2 | 6/2010 | Borst |
| 7,780,460 B2 | 8/2010 | Walter |
| 7,787,132 B2 | 8/2010 | Korner et al. |
| 7,791,810 B2 | 9/2010 | Powell |
| 7,796,243 B2 | 9/2010 | Choo-Smith et al. |
| 7,806,727 B2 | 10/2010 | Dold et al. |
| 7,813,787 B2 | 10/2010 | de Josselin de Jong et al. |
| 7,824,180 B2 | 11/2010 | Abolfathi et al. |
| 7,828,601 B2 | 11/2010 | Pyczak |
| 7,845,969 B2 | 12/2010 | Stadler et al. |
| 7,854,609 B2 | 12/2010 | Chen et al. |
| 7,862,336 B2 | 1/2011 | Kopelman et al. |
| 7,872,760 B2 | 1/2011 | Ertl |
| 7,874,836 B2 | 1/2011 | McSurdy, Jr. |
| 7,874,849 B2 | 1/2011 | Sticker et al. |
| 7,878,801 B2 | 2/2011 | Abolfathi et al. |
| 7,907,280 B2 | 3/2011 | Johs et al. |
| 7,929,151 B2 | 4/2011 | Liang et al. |
| 7,947,508 B2 | 5/2011 | Tricca et al. |
| 7,959,308 B2 | 6/2011 | Freeman et al. |
| 7,963,766 B2 | 6/2011 | Cronauer |
| 7,986,415 B2 | 7/2011 | Thiel et al. |

(56) References Cited

U.S. PATENT DOCUMENTS

| | | |
|---|---|---|
| 8,017,891 B2 | 9/2011 | Nevin |
| 8,026,916 B2 | 9/2011 | Wen |
| 8,027,709 B2 | 9/2011 | Arnone et al. |
| 8,054,556 B2 | 11/2011 | Chen et al. |
| 8,077,949 B2 | 12/2011 | Liang et al. |
| 8,083,556 B2 | 12/2011 | Stadler et al. |
| D652,799 S | 1/2012 | Mueller |
| 8,118,592 B2 | 2/2012 | Tortorici |
| 8,126,025 B2 | 2/2012 | Takeda |
| 8,144,954 B2 | 3/2012 | Quadling et al. |
| 8,160,334 B2 | 4/2012 | Thiel et al. |
| 8,201,560 B2 | 6/2012 | Dembro |
| 8,215,312 B2 | 7/2012 | Garabadian et al. |
| 8,240,018 B2 | 8/2012 | Walter et al. |
| 8,279,450 B2 | 10/2012 | Oota et al. |
| 8,292,617 B2 | 10/2012 | Brandt et al. |
| 8,294,657 B2 | 10/2012 | Kim et al. |
| 8,297,286 B2 | 10/2012 | Smernoff |
| 8,306,608 B2 | 11/2012 | Mandelis et al. |
| 8,310,683 B2 | 11/2012 | Babayoff et al. |
| 8,314,764 B2 | 11/2012 | Kim et al. |
| 8,332,015 B2 | 12/2012 | Ertl |
| 8,354,588 B2 | 1/2013 | Sticker et al. |
| 8,363,228 B2 | 1/2013 | Babayoff |
| 8,366,479 B2 | 2/2013 | Borst et al. |
| 8,465,280 B2 | 6/2013 | Sachdeva et al. |
| 8,477,320 B2 | 7/2013 | Stock et al. |
| 8,488,113 B2 | 7/2013 | Thiel et al. |
| 8,520,922 B2 | 8/2013 | Wang et al. |
| 8,520,925 B2 | 8/2013 | Duret |
| 8,556,625 B2 | 10/2013 | Lovely |
| 8,570,530 B2 * | 10/2013 | Liang .................. A61B 1/00009 356/601 |
| 8,573,224 B2 | 11/2013 | Thornton |
| 8,577,212 B2 | 11/2013 | Thiel |
| 8,594,408 B2 | 11/2013 | Alpern et al. |
| 8,650,586 B2 | 2/2014 | Lee et al. |
| 8,675,706 B2 | 3/2014 | Seurin et al. |
| 8,723,029 B2 | 5/2014 | Pyczak et al. |
| 8,743,923 B2 | 6/2014 | Geske et al. |
| 8,767,270 B2 | 7/2014 | Curry et al. |
| 8,768,016 B2 | 7/2014 | Pan et al. |
| 8,771,149 B2 | 7/2014 | Rahman et al. |
| 8,839,476 B2 | 9/2014 | Adachi |
| 8,870,566 B2 | 10/2014 | Bergersen |
| 8,878,905 B2 | 11/2014 | Fisker et al. |
| 8,899,976 B2 | 12/2014 | Chen et al. |
| 8,936,463 B2 | 1/2015 | Mason et al. |
| 8,948,482 B2 | 2/2015 | Levin |
| 8,956,058 B2 | 2/2015 | Rosch |
| 8,992,216 B2 | 3/2015 | Karazivan |
| 9,022,792 B2 | 5/2015 | Sticker et al. |
| 9,039,418 B1 | 5/2015 | Rubbert |
| 9,084,535 B2 | 7/2015 | Girkin et al. |
| 9,108,338 B2 | 8/2015 | Sirovskiy et al. |
| 9,144,512 B2 | 9/2015 | Wagner |
| 9,192,305 B2 | 11/2015 | Levin |
| 9,204,952 B2 | 12/2015 | Lampalzer |
| 9,242,118 B2 | 1/2016 | Brawn |
| 9,261,358 B2 | 2/2016 | Atiya et al. |
| 9,299,192 B2 | 3/2016 | Kopelman |
| 9,336,336 B2 | 5/2016 | Deichmann et al. |
| 9,408,743 B1 | 8/2016 | Wagner |
| 9,433,476 B2 | 9/2016 | Khardekar et al. |
| 9,439,568 B2 | 9/2016 | Atiya et al. |
| 9,444,981 B2 | 9/2016 | Bellis et al. |
| 9,500,635 B2 | 11/2016 | Islam |
| 9,506,808 B2 | 11/2016 | Jeon et al. |
| 9,513,470 B1 | 12/2016 | Weaver |
| 9,545,331 B2 | 1/2017 | Ingemarsson-Matzen |
| 9,584,771 B2 | 2/2017 | Mandelis et al. |
| 9,675,430 B2 | 6/2017 | Verker et al. |
| 9,693,839 B2 | 7/2017 | Atiya et al. |
| 9,744,006 B2 | 8/2017 | Ross |
| 9,936,186 B2 | 4/2018 | Jesenko et al. |
| 2001/0038705 A1 | 11/2001 | Rubbert et al. |
| 2002/0010568 A1 | 1/2002 | Rubbert et al. |
| 2002/0015934 A1 | 2/2002 | Rubbert et al. |
| 2003/0009252 A1 | 1/2003 | Pavlovskaia et al. |
| 2003/0048540 A1 | 3/2003 | Xie et al. |
| 2003/0139834 A1 | 7/2003 | Nikolskiy et al. |
| 2003/0190575 A1 | 10/2003 | Hilliard |
| 2003/0207224 A1 | 11/2003 | Lotte |
| 2003/0224311 A1 | 12/2003 | Cronauer |
| 2004/0009449 A1 | 1/2004 | Mah et al. |
| 2004/0019262 A1 | 1/2004 | Perelgut |
| 2004/0058295 A1 | 3/2004 | Bergersen |
| 2004/0090638 A1 | 5/2004 | Babayoff |
| 2004/0094165 A1 | 5/2004 | Cook |
| 2005/0031196 A1 | 2/2005 | Moghaddam et al. |
| 2005/0037312 A1 | 2/2005 | Uchida |
| 2005/0048433 A1 | 3/2005 | Hilliard |
| 2005/0100333 A1 | 5/2005 | Kerschbaumer et al. |
| 2005/0181333 A1 | 8/2005 | Karazivan et al. |
| 2005/0186524 A1 | 8/2005 | Abolfathi et al. |
| 2005/0244781 A1 | 11/2005 | Abels et al. |
| 2006/0001739 A1 * | 1/2006 | Babayoff .......... A61B 1/00009 348/49 |
| 2006/0084024 A1 | 4/2006 | Farrell |
| 2006/0099546 A1 | 5/2006 | Bergersen |
| 2006/0154198 A1 | 7/2006 | Durbin et al. |
| 2006/0223032 A1 | 10/2006 | Fried et al. |
| 2006/0223342 A1 | 10/2006 | Borst et al. |
| 2006/0234179 A1 | 10/2006 | Wen et al. |
| 2007/0046865 A1 | 3/2007 | Umeda et al. |
| 2007/0053048 A1 | 3/2007 | Kumar et al. |
| 2007/0087300 A1 | 4/2007 | Willison et al. |
| 2007/0184402 A1 | 8/2007 | Boutoussov et al. |
| 2007/0231765 A1 | 10/2007 | Phan et al. |
| 2007/0296959 A1 | 12/2007 | Schwotzer |
| 2008/0045053 A1 | 2/2008 | Stadler et al. |
| 2008/0062429 A1 | 3/2008 | Liang et al. |
| 2008/0063998 A1 * | 3/2008 | Liang .................. A61B 1/0638 433/29 |
| 2008/0090208 A1 | 4/2008 | Rubbert |
| 2008/0115791 A1 | 5/2008 | Heine |
| 2008/0176448 A1 | 7/2008 | Muller et al. |
| 2008/0242144 A1 | 10/2008 | Dietz |
| 2009/0030347 A1 | 1/2009 | Cao |
| 2009/0040740 A1 | 2/2009 | Muller et al. |
| 2009/0061379 A1 | 3/2009 | Yamamoto et al. |
| 2009/0061381 A1 | 3/2009 | Durbin et al. |
| 2009/0075228 A1 | 3/2009 | Kumada et al. |
| 2009/0210032 A1 | 8/2009 | Beiski et al. |
| 2009/0218514 A1 | 9/2009 | Klunder et al. |
| 2009/0298017 A1 | 12/2009 | Boerjes et al. |
| 2009/0305540 A1 | 12/2009 | Stadler et al. |
| 2010/0045902 A1 | 2/2010 | Ikeda et al. |
| 2010/0085636 A1 | 4/2010 | Berner |
| 2010/0152599 A1 | 6/2010 | DuHamel et al. |
| 2010/0165275 A1 | 7/2010 | Tsukamoto et al. |
| 2010/0167225 A1 | 7/2010 | Kuo |
| 2010/0231577 A1 | 9/2010 | Kim et al. |
| 2010/0312484 A1 | 12/2010 | DuHamel et al. |
| 2011/0045428 A1 | 2/2011 | Boltunov et al. |
| 2011/0081625 A1 | 4/2011 | Fuh |
| 2011/0102549 A1 | 5/2011 | Takahashi |
| 2011/0102566 A1 | 5/2011 | Zakian et al. |
| 2011/0143673 A1 | 6/2011 | Landesman et al. |
| 2011/0229840 A1 * | 9/2011 | Liang .................. A61B 5/1077 433/29 |
| 2011/0235045 A1 | 9/2011 | Koerner et al. |
| 2011/0269092 A1 | 11/2011 | Kuo et al. |
| 2012/0081786 A1 | 4/2012 | Mizuyama et al. |
| 2012/0086681 A1 | 4/2012 | Kim et al. |
| 2012/0092461 A1 | 4/2012 | Fisker et al. |
| 2012/0129117 A1 | 5/2012 | McCance |
| 2012/0147912 A1 | 6/2012 | Moench et al. |
| 2012/0172678 A1 | 7/2012 | Logan et al. |
| 2012/0281293 A1 | 11/2012 | Gronenborn et al. |
| 2012/0295216 A1 | 11/2012 | Dykes et al. |
| 2012/0322025 A1 | 12/2012 | Ozawa et al. |
| 2013/0089828 A1 | 4/2013 | Borovinskih et al. |
| 2013/0095446 A1 | 4/2013 | Andreiko et al. |

(56) References Cited

U.S. PATENT DOCUMENTS

| | | |
|---|---|---|
| 2013/0103176 A1 | 4/2013 | Kopelman et al. |
| 2013/0110469 A1 | 5/2013 | Kopelman |
| 2013/0163627 A1 | 6/2013 | Seurin et al. |
| 2013/0201488 A1 | 8/2013 | Ishihara |
| 2013/0235165 A1 | 9/2013 | Gharib et al. |
| 2013/0252195 A1 | 9/2013 | Popat |
| 2013/0266326 A1 | 10/2013 | Joseph et al. |
| 2013/0280671 A1 | 10/2013 | Brawn et al. |
| 2013/0286174 A1 | 10/2013 | Urakabe |
| 2013/0293824 A1 | 11/2013 | Yoneyama et al. |
| 2013/0323664 A1 | 12/2013 | Parker |
| 2013/0323671 A1 | 12/2013 | Dillon et al. |
| 2013/0323674 A1 | 12/2013 | Hakomori et al. |
| 2014/0081091 A1 | 3/2014 | Abolfathi et al. |
| 2014/0272774 A1 | 9/2014 | Dillon et al. |
| 2014/0294273 A1 | 10/2014 | Jaisson |
| 2014/0313299 A1 | 10/2014 | Gebhardt et al. |
| 2014/0329194 A1 | 11/2014 | Sachdeva et al. |
| 2014/0363778 A1 | 12/2014 | Parker |
| 2015/0002649 A1 | 1/2015 | Nowak et al. |
| 2015/0029309 A1 | 1/2015 | Michaeli et al. |
| 2015/0079531 A1 | 3/2015 | Heine |
| 2015/0140502 A1 | 5/2015 | Brawn et al. |
| 2015/0164335 A1 | 6/2015 | Van Der Poel et al. |
| 2015/0173856 A1 | 6/2015 | Lowe et al. |
| 2015/0230885 A1 | 8/2015 | Wucher |
| 2015/0238280 A1 | 8/2015 | Wu et al. |
| 2015/0238283 A1 | 8/2015 | Tanugula et al. |
| 2015/0306486 A1 | 10/2015 | Logan et al. |
| 2015/0320320 A1 | 11/2015 | Kopelman et al. |
| 2015/0325044 A1 | 11/2015 | Lebovitz |
| 2015/0338209 A1 | 11/2015 | Knuttel |
| 2016/0000332 A1 | 1/2016 | Atiya et al. |
| 2016/0003610 A1 | 1/2016 | Lampert et al. |
| 2016/0045291 A1* | 2/2016 | Verker ............ A61C 9/0066 356/364 |
| 2016/0051345 A1 | 2/2016 | Levin |
| 2016/0064898 A1 | 3/2016 | Atiya et al. |
| 2016/0067013 A1 | 3/2016 | Morton et al. |
| 2016/0081768 A1 | 3/2016 | Kopelman et al. |
| 2016/0081769 A1 | 3/2016 | Kimura et al. |
| 2016/0135924 A1 | 5/2016 | Choi et al. |
| 2016/0135925 A1 | 5/2016 | Mason et al. |
| 2016/0163115 A1 | 6/2016 | Furst |
| 2016/0217708 A1 | 7/2016 | Levin et al. |
| 2016/0296303 A1 | 10/2016 | Parker |
| 2016/0328843 A1 | 11/2016 | Graham et al. |
| 2016/0330355 A1 | 11/2016 | Tchouprakov et al. |
| 2017/0007366 A1 | 1/2017 | Kopelman et al. |
| 2017/0007367 A1 | 1/2017 | Li et al. |
| 2017/0049311 A1 | 2/2017 | Borovinskih et al. |
| 2017/0049326 A1 | 2/2017 | Alfano et al. |
| 2017/0056131 A1 | 3/2017 | Alauddin et al. |
| 2017/0156821 A1 | 6/2017 | Kopelman et al. |
| 2017/0265970 A1 | 9/2017 | Verker et al. |
| 2017/0325690 A1 | 11/2017 | Salah et al. |
| 2018/0000563 A1 | 1/2018 | Shanjani et al. |
| 2018/0000565 A1 | 1/2018 | Shanjani et al. |
| 2018/0028063 A1 | 2/2018 | Elbaz et al. |
| 2018/0028064 A1 | 2/2018 | Elbaz et al. |
| 2018/0028065 A1 | 2/2018 | Elbaz et al. |
| 2018/0055602 A1 | 3/2018 | Kopelman et al. |
| 2018/0125610 A1 | 5/2018 | Carrier, Jr. et al. |
| 2018/0153648 A1 | 6/2018 | Shanjani et al. |
| 2018/0153649 A1 | 6/2018 | Wu et al. |
| 2018/0153733 A1 | 6/2018 | Kuo |
| 2018/0280118 A1 | 10/2018 | Cramer |
| 2018/0284727 A1 | 10/2018 | Cramer et al. |

FOREIGN PATENT DOCUMENTS

| | | |
|---|---|---|
| AU | 9150082 A | 6/1984 |
| AU | 5598894 A | 6/1994 |
| CA | 1121955 A1 | 4/1982 |
| CN | 102802520 A | 11/2012 |
| DE | 2749802 A1 | 5/1978 |
| DE | 69327661 T2 | 7/2000 |
| DE | 102005043627 A1 | 3/2007 |
| DE | 202010017014 U1 | 3/2011 |
| DE | 102011051443 A1 | 1/2013 |
| DE | 102014225457 A1 | 6/2016 |
| EP | 0428152 A1 | 5/1991 |
| EP | 490848 A2 | 6/1992 |
| EP | 541500 A1 | 5/1993 |
| EP | 0714632 B1 | 5/1997 |
| EP | 774933 B1 | 12/2000 |
| EP | 731673 B1 | 5/2001 |
| EP | 1941843 A2 | 7/2008 |
| EP | 2213223 A1 | 8/2010 |
| EP | 2437027 A2 | 4/2012 |
| EP | 2447754 A1 | 5/2012 |
| EP | 1989764 B1 | 7/2012 |
| EP | 2332221 B1 | 11/2012 |
| EP | 2596553 B1 | 12/2013 |
| EP | 2612300 B1 | 2/2015 |
| EP | 2848229 A1 | 3/2015 |
| ES | 463897 A1 | 1/1980 |
| ES | 2455066 A1 | 4/2014 |
| FR | 2369828 A1 | 6/1978 |
| FR | 2930334 A1 | 10/2009 |
| GB | 1550777 A | 8/1979 |
| JP | H53-058191 A | 5/1978 |
| JP | 04-258359 A | 1/1992 |
| JP | H08-508174 A | 9/1996 |
| JP | 63-11148 | 1/1998 |
| JP | 2002-522752 A | 7/2002 |
| JP | 2003290133 A | 10/2003 |
| JP | 2007-260158 A | 10/2007 |
| JP | 2008-523370 A | 7/2008 |
| JP | 04184427 B1 | 11/2008 |
| JP | 2009-000412 A | 1/2009 |
| JP | 2009-018173 A | 1/2009 |
| JP | 2011-087733 A | 5/2011 |
| JP | 2012-526977 A | 11/2012 |
| JP | 2013-007645 A | 1/2013 |
| JP | 2016528972 A | 9/2016 |
| KR | 10-1266966 B1 | 5/2013 |
| KR | 10-2016-041632 A | 4/2016 |
| KR | 10-2016-0071127 A | 6/2016 |
| WO | 91-004713 A1 | 4/1991 |
| WO | 94-010935 A1 | 5/1994 |
| WO | 98-032394 A1 | 7/1998 |
| WO | 98-044865 A1 | 10/1998 |
| WO | 2000/08415 A1 | 2/2000 |
| WO | 2002-017776 A2 | 3/2002 |
| WO | 2002-062252 A1 | 8/2002 |
| WO | 2002-095475 A1 | 11/2002 |
| WO | 2003-003932 A2 | 1/2003 |
| WO | 2006-096558 A2 | 9/2006 |
| WO | 2006-133548 A1 | 12/2006 |
| WO | 2009-085752 A2 | 7/2009 |
| WO | 2009-089129 A1 | 7/2009 |
| WO | 2009-146788 A1 | 12/2009 |
| WO | 2009-146789 A1 | 12/2009 |
| WO | 2012-007003 A1 | 1/2012 |
| WO | 2012-064684 A2 | 5/2012 |
| WO | 2012-074304 A2 | 6/2012 |
| WO | 2014-091865 A1 | 6/2014 |
| WO | 2015-015289 A2 | 2/2015 |
| WO | 2015-015289 A2 | 2/2015 |
| WO | 2015-063032 A1 | 5/2015 |
| WO | 2015-176004 A1 | 11/2015 |
| WO | 2016-004415 A1 | 1/2016 |
| WO | 2016-042393 A1 | 3/2016 |
| WO | 2016-061279 A1 | 4/2016 |
| WO | 2016-084066 A1 | 6/2016 |
| WO | 2016-099471 A1 | 6/2016 |
| WO | 2016-113745 A1 | 7/2016 |

(56) References Cited

FOREIGN PATENT DOCUMENTS

| | | |
|---|---|---|
| WO | 2016-116874 A1 | 7/2016 |
| WO | 2018-085718 A2 | 5/2018 |

OTHER PUBLICATIONS

Kochanek et al., "Interpolating Splines with Local Tension, Continuity and Bias Control", Computer Graphics; 18(3); pp. 33-41; Jan. 1, 1984.

Kumar et al.; Rapid maxillary expansion: A unique treatment modality in dentistry; J. Clin. Diagn. Res.; 5(4); pp. 906-911; Aug. 2011.

Kunii et al., "Articulation Simulation for an Intelligent Dental Care System" Displays; 15(3); pp. 181-188; Jul. 1994.

Kuroda et al., "Three-Dimensional Dental Cast Analyzing System Using Laser Scanning", American Journal of Orthodontics and Dentofacial Orthopedics; 11 0(4 ); pp. 365-369; Oct. 1996.

Laurendeau et al., "A Computer-Vision Technique for the Acquisition and Processing of 3-D Profiles of Dental Imprints: An Application in Orthodontics", IEEE Transactions on Medical Imaging; 1 0(3); pp. 453-461; Sep. 1991.

Leinfelder et al., "A New Method for Generating Ceramic Restorations: a CAD-CAM System" Journal of the American Dental Association; 118(6); pp. 703-707; Jun. 1989.

Manetti et al., "Computer-Aided Cefalometry and New Mechanics in Orthodontics" Fortschr Kieferorthop; 44; pp. 370-376; 8 pages; (English Article Summary Included); (year of pub. sufficiently earlier than effective US filing date and any foreign priority date) 1983.

McCann; Inside the ADA; J. Amer. Dent. Assoc, 118:286-294; Mar. 1989.

McNamara et al., "Invisible Retainers", J. Clin Orthod.; pp. 570-578; 11 pages; (Author Manuscript); Aug. 1985.

McNamara et al.; "Orthodontic and Orthopedic Treatment in the Mixed Dentition", Needham Press; pp. 347-353; Jan. 1993.

Moermann et al, "Computer Machined Adhesive Porcelain Inlays: Margin Adaptation after Fatigue Stress", IADR Abstract 339; J. Dent. Res.; 66(a):763; (Abstract Only); (year of pub. sufficiently earlier than effective US filing date and any foreign priority date) 1987.

Moles, "Correcting Mild Malalignments—As Easy As One, Two, Three", AOA/Pro Corner; 11 (2); 2 pages; (year of pub. sufficiently earlier than effective US filing date and any foreign priority date) 2002.

Mormann et al.; "Marginale Adaptation von adhasuven Porzellaninlays in vitro", Separatdruck aus:Schweiz. Mschr. Zahnmed.; 95; pp. 1118-1129: 8 pages; (Machine Translated English Abstract); (year of pub. sufficiently earlier than effective US filing date and any foreign priority date); 1985.

Nahoum, "The Vacuum Formed Dental Contour Appliance", N.Y. State Dent. J.; 30(9); pp. 385-390; Nov. 1964.

Nash, "CEREC CAD/CAM Inlays: Aesthetics and Durability in a Single Appointment", Dentistry Today; 9(8); pp. 20, 22-23 and 54; Oct. 1990.

Nedelcu et al.; "Scanning Accuracy and Precision in 4 Intraoral Scanners: An In Vitro Comparison Based on 3-Dimensional Analysis"; J. Prosthet. Dent.; 112(6); pp. 1461-1471; Dec. 2014.

Nishiyama et al., "A New Construction of Tooth Repositioner by LTV Vinyl Silicone Rubber", Journal of Nihon University School of Dentistry; 19(2); pp. 93-102 (year of pub. Sufficiently earlier than effective US filing date and any foreign priority date) 1977.

Ogawa et al., "Mapping, profiling and clustering of pressure pain threshold (PPT) in edentulous oral muscosa", Journal of Dentistry; 32(3); pp. 219-228; Mar. 2004.

Ogimoto et al., "Pressure-pain threshold determination in the oral mucosa: validity and reliability", Journal of Oral Rehabilitation; 29(7); pp. 620-626; Jul. 2002.

Paul et al.; "Digital Documentation of Individual Human Jaw and Tooth Forms for Applications in Orthodontics; Oral Surgery and Forensic Medicine" Proc. of the 24th Annual Conf. of the IEEE Industrial Electronics Society (IECON '98); vol. 4; pp. 2415-2418; Sep. 4, 1998.

Pinkham, "'Foolish' Concept Propels Technology", Dentist, 3 pages, Jan./Feb. 1989.

Pinkham, "Inventor's CAD/CAM May Transform Dentistry", Dentist; pp. 1 and 35, Sep. 1990.

Ponitz, "Invisible Retainers", American Journal of Orthodics, 59(3); pp. 266-272; Mar. 1971.

Procera Research Projects; Procera Research Projects 1993. Abstract Collection; 23 pages; (year of pub. sufficiently earlier than effective US filing date and any foreign priority date) 1993.

Proffit et al., "The First Stage of Comprehensive Treatment: Alignment and Leveling", Contemporary Orthodontics, 3rd Ed.; Chapter 16; Mosby Inc.; pp. 534-537; (year of pub. sufficiently earlier than effective US filing date and any foreign priority date) 2000.

Proffit et al.; "The First Stage of Comprehensive Treatment: Alignment and Leveling", Contemporary Orthodontics; (Second Ed.); Chapter 15, MosbyYear Book; St. Louis, Missouri; pp. 470-533 Oct. 1993.

Raintree Essix & ARS Materials, Inc., Raintree Essix, Technical Magazine Table of contents and Essix Appliances, 7 pages; retrieved from the internet (http:llwww.essix.com.lmagazineldefaulthtml) on Aug. 13, 1997.

Redmond et al.; "Clinical Implications of Digital Orthodontics", American Journal of Orthodontics and Dentofacial Orthopedics; 117(2); pp. 240-242; Feb. 2000.

Rekow et al., "CAD/CAM for Dental Restorations—Some of the Curious Challenges", IEEE Transactions on Biomedical Engineering; 38(4); pp. 314-318; Apr. 1991.

Rekow et al., "Comparison of Three Data Acquisition Techniques for 3-D Tooth Surface Mapping", Annual International Conference of the IEEE Engineering in Medicine and Biology Society; 13(1); pp. 344-345 (year of pub. sufficiently earlier than effective US filing date and any foreign priority date) 1991.

Rekow, "A Review of the Developments in Dental CAD/CAM Systems", Current Opinion in Dentistry; pp. 25-33; Jun. 1992.

Rekow, "CAD/CAM in Dentistry: A Historical Perspective and View of the Future", Journal Canadian Dental Association; 58(4); pp. 283, 287-288; Apr. 1992.

Rekow, "Computer-Aided Design and Manufacturing in Dentistry: A Review of the State of the Art", Journal of Prosthetic Dentistry; 58(4 ); pp. 512-516; Dec. 1987.

Rekow, "Dental CAD-CAM Systems: What is the State of the Art?", The Journal of the American Dental Association; 122(12); pp. 43-48; Dec. 1991.

Rekow, "Feasibility of an Automated System for Production of Dental Restorations", Ph.D. Thesis; Univ. of Minnesota, 250 pages, Nov. 1988.

Richmond et al., "The Development of a 3D Cast Analysis System", British Journal of Orthodontics; 13(1 ); pp. 53-54; Jan. 1986.

Richmond et al., "The Development of the PAR Index (Peer Assessment Rating): Reliability and Validity", The European Journal of Orthodontics; 41(2); pp. 125-139; Apr. 1992.

Richmond, "Recording the Dental Cast in Three Dimensions", American Journal of Orthodontics and Dentofacial Orthopedics; 92(3); pp. 199-206; Sep. 1987.

Rudge, "Dental Arch Analysis: Arch Form, A Review of the Literature" European Journal of Orthodontics; 3(4 ); pp. 279-284; Jan. 1981.

Sahm et al, "Micro-Electronic Monitoring of Functional Appliance Wear"; Eur J Orthod.; 12(3); pp. 297-301; Aug. 1990.

Sahm, "Presentation of a wear timer for the clarification of scientific questions in orthodontic orthopedics", Fortschritte der Kieferorthopadie; 51 (4); pp. 243-247; (Translation Included) Jul. 1990.

Sakuda et al. "Integrated Information-Processing System in Clinical Orthodontics: An Approach with Use of a Computer Network System", American Journal of Orthodontics and Dentofacial Orthopedics; 101 (3); pp. 210-220; 20 pages; (Author Manuscript) Mar. 1992.

(56) References Cited

OTHER PUBLICATIONS

Schafer et al.; "Quantifying patient adherence during active orthodontic treatment with removable appliances using microelectronic wear-time documentation"; Eur J Orthod.; 37(1) pp. 1-8; doi:10.1093/ejo/cju012; Jul. 3, 2014.
Schellhas et al., "Three-Dimensional Computed Tomography in Maxillofacial Surgical Planning", Archives of Otolaryngology—Head and Neck Surgery; 114(4); pp. 438-442; Apr. 1988.
Schroeder et al; Eds. "The Visual Toolkit", Prentice Hall PTR, New Jersey; Chapters 6, 8 & 9, (pp. 153-210,309-354, and 355-428; (year of pub. sufficiently earlier than effective US filing date and any foreign priority date) 1998.
Shilliday, "Minimizing finishing problems with the mini-positioner", American Journal of Orthodontics; 59(6); pp. 596-599; Jun. 1971.
Shimada et al.; Application of Optical Coherence Tomography (OCT) for Diagnosis of Caries, Cracks, and Defects of Restorations, Current Oral Health Reports; 2(2); pp. 73-80; Jun. 2015.
International Search Report and Written Opinion for PCT Application No. PCT/IB2015/054950 dated Apr. 1, 2016.
International Preliminary Report on Patentability and Written Opinion for International Application No. PCT/IB2015/054950 dated Jan. 10, 2017.
IP Australia, Examination Report No. 1 for Patent Application No. 2015287312 dated Jul. 31, 2017, 4 pages.2018, 5 pages.
IP Australia, Examination Report No. 2 for Patent Application No. 2015287312 dated Feb. 12, 2018, 4 pages.2018, 4 pages.
Canadian Intellectual Property Office, Office Action for Canadian Patent Application No. 2,949,448 dated Sep. 26, 2017, 3 pages.
Japanese Patent Office, Office Action for Japanese Patent Application No. JP 2017-500896 dated May 29, 2018.
Korean Intellectual Property Office, Notification of Reason for Refusal for Korean Patent Application No. 10-2017-7003299 dated Nov. 14, 2017, including English translation, 15 pages.
International Search Report and Written Opinion for International Patent Application No. PCT/US2018/013321 dated Apr. 26, 2018, 16 pages.
AADR, American Association for Dental Research; Summary of Activities; Los Angeles, CA; p. 195; Mar. 20-23, 1980.
Alcaniz et al., "An Advanced System for the Simulation and Planning of Orthodontic Treatments" Visualization in Biomedical Computing, 4th Intl. Conf, VBC '96, Sep. 22-25, 1996, pp. 511-520, Springer-Verlag, Hamburg, Germany.
Alexander et al., "The DigiGraph Work Station Part 2 Clinical Management", J. Clin. Orthod., Jul. 1990, 12 pages.
Allesee Orthodontic Appliances: "Important Tip About Wearing the Red White & Blue Active Clear Retainer System", Allesee Orthodontic Appliances—Pro Lab; 1 page; (year of pub. Sufficiently earlier than effecitve US filing date and any foreign priroirty date); 1998.
Allesee Orthodontic Appliances; The Choice is Clear: Red, White & Blue . . . the Simple, Affordable, No-Braces Treatment; (Patient Information); retrieved from the internet (http://ormco.com/aoa/appliancesservices/RWB/patients.html); 2 pages on May 19, 2003.
Allesee Orthodontic Appliances; The Choice is Clear: Red, White & Blue . . . the Simple, Affordable, No-Braces Treatment; (product information for doctors); retrieved from the internet (http://ormco.com/aoa/appliancesservices/RWB/doctrohtml); 5 pages on May 19, 2003.
Allesee Orthodontic Appliances; The Choice is Clear: Red, White & Blue . . . the Simple, Affordable, No-Braces Treatment; (product information), 6 pages; (year of pub. Sufficiently earlier than effective US filing date and any foreign priority date) 2003.
Allesee Orthodontic Appliances; The Red, White & Blue Way to Improve Your Smile; (information for patients), 2 pages; (year of pub. Sufficiently earlier than effective US filing date and any foreign priority date) 1992.
Allesee Orthodontic Appliances; You may be a candidate for this invisible no-braces treatment; product information for patients; 2 pages; (year of pub. Sufficiently earlier than effective US filing date and any foreign priority date) 2002.
Allesee Orthodontic Applicances: Dura ClearTM; Product information; 1 page; (year of pub. Sufficiently earlier than effective US filing date and any foreign priority date) 1997.
Altschuler et al., Analysis of 3-D Data for Comparative 3-D Serial Growth Pattern Studies of Oral-Facial Structures; IADR Abstracts, Program and Abstracts of Papers, 57th General Session, AIDR Annual Session, Mar. 29, 1979-Apr. 1, 1979, New Orleans Marriot; Journal of Dental Research; vol. 58, Special Issue A, p. 221; Jan. 1979.
Altschuler et al., Laser Electro-Optic System for Rapid Three-Dimensional (3D) Topographic Mapping of Surfaces; Optical Engineering; Dec. 1981, pp. 953-961, vol. 20(6).
Altschuler et al., "Measuring Surfaces Space-Coded by a Laser-Projected Dot Matrix" SPIE Imaging Applications for Automated Industrial Inspection and Assembly; Oct. 10, 1979, pp. 187-191, vol. 182.
Altschuler; 3D Mapping of Maxillo-Facial Prosthesis; AADR Abstract #607; 1 page, (year of pub. sufficiently earlier than effective US filing date and any foreign priority date) 1980.
Andersson et al.; Clinical Results with Titanium Crowns Fabricated with Machine Duplication and Spark Erosion; Acta Odontologica Scandinavica; 47(5); pp. 279-286; Oct. 1989.
Andrews, "The Six Keys to Optimal Occlusion" Straight Wire, Chapter 3, L.A. Wells; pp. 13-24; (year of pub. sufficiently earlier than effective US filing date and any foreign priority date) 1989.
Barone et al., "Creation of 30 Multi-Body Orthodontic Models by Using Independent Imaging Sensors"; Sensors; 13(2); pp. 2033-2050; Feb. 5, 2013.
Bartels et al.; An Introduction to Splines for Use in Computer Graphics and Geometric Modeling; Morgan Kaufmann Publishers; pp. 422-425 Jan. 1, 1987.
Baumrind et al, "Mapping the Skull in 3-D," reprinted from J. Calif. Dent. Assoc, 48(2), 11 pages; (year of pub. sufficiently earlier than effective US filing date and any foreign priority date) Fall Issue 1972, vol. 48, No. 2.
Baumrind et al., "A Stereophotogrammetric System for the Detection of Prosthesis Loosening in Total Hip Arthroplasty", NATO Symposium on Applications of Human Biostereometrics; SPIE; vol. 166; pp. 112-123; Jul. 9-13, 1978.
Baumrind, "A System for Crania facial Mapping Through the Integration of Data from Stereo X-Ray Films and Stereo Photographs", an invited paper submitted to the 1975 American Society of Photogram Symposium on Close-Range Photogram Systems; University of Illinois; pp. 142-166; Aug. 26-30, 1975.
Baumrind, "Integrated Three-Dimensional Craniofacial Mapping: Background, Principles, and Perspectives", Seminars in Orthodontics; 7(4 ); pp. 223-232; Dec. 2001.
Begole et al.; A Computer System for the Analysis of Dental Casts; The Angle Orthodontist; 51(3); pp. 252-258, Jul. 1981.
Bernard et al, "Computerized Diagnosis in Orthodontics for Epidemiological Studies: A ProgressReport" (Abstract Only), J. Dental Res. Special Issue, vol. 67, p. 169, paper presented at International Association for Dental Research 66th General Session, Montreal Canada; Mar. 9-13, 1988.
Bhatia et al., "A Computer-Aided Design for Orthognathic Surgery", British Journal of Oral and Maxillofacial Surgery; 22(4 ); pp. 237-253; Aug. 1, 1984.
Biggerstaff et al., "Computerized Analysis of Occlusion in the Postcanine Dentition", American Journal of Orthodontics; 61 (3); pp. 245-254; Mar. 1972.
Biggerstaff, "Computerized Diagnostic Setups and Simulations", Angle Orthodontist; 40(I); pp. 28-36; Jan. 1970.
Biostar Operation & Training Manual. Great Lakes Orthodontics, Ltd. 199 Fire Tower Drive, Tonawanda, New York. 14150-5890, 20 pages; (year of pub. sufficiently earlier than effective US filing date and any foreign priority date) 1990.
Blu et al.; "Linear Interpolation Revitalized", IEEE Transactions on Image Processing; 13(5); pp. 710-719; May 2004.
Bourke, "Coordinate System Transformation", 2 pages, Jun. 1996, retrieved from the internet (http://local.wasp.uwa.edu.au/~pbourke/protection/coords/) on Sep. 19, 2006.

(56) References Cited

OTHER PUBLICATIONS

Boyd et al., "Three Dimensional Diagnosis and Orthodontic Treatment of Complex Malocclusions With the Invisalipn Appliance", Seminars in Orthodontics; 7(4); pp. 274-293; Dec. 2001.
Brandestini et al. "Computer Machined Ceramic Inlays: In Vitro Marginal Adaptation", J. Dent. Res. Special Issue; (Abstract 305); vol. 64; p. 208; (year of pub. sufficiently earlier than effective US filing date and any foreign priority date) 1985.
Brook et al., "An Image Analysis System for the Determination of Tooth Dimensions from Study Casts: Comparison with Manual Measurements of Mesio-distal Diameter", Journal of Dental Research; 65(3); pp. 428-431: Mar. 1986.
Burstone et al., "Precision Adjustment of the Transpalatal Lingual Arch: Computer Arch Form Predetermination", American Journal of Orthodontics; 79(2);pp. 115-133; Feb. 1981.
Burstone; "Dr. Charles J. Burstone on the Uses of the Computer in Orthodontic Practice (Part 1 )"; Journal of Clinical Orthodontics; 13(7); pp. 442-453; (interview); Jul. 1979.
Burstone; "Dr. Charles J. Burstone on The Uses of the Computer in Orthodontic Practice (Part 2)"; Journal of Clinical Orthodontics; 13(8); pp. 539-551 (interview); Aug. 1979.
"Cardinal Industrial Finishes for Liquid and Powder Coatings", The Powder Coating Isntitute; 6 pages; retrieved from the internet (http://www.cardinalpaint.com/powder%20coatings.htm) on Aug. 25, 2000.
Carnaghan et al., "An Alternative to Holograms for the Portrayal of Human Teeth", 4th Int'l. Conf. on Holographic Systems, Components and Applications; pp. 228-231; Sep. 15, 1993.
Chaconas et al, "The DigiGraph Work Station, Part 1, Basic Concepts"; Journal of Clinical Orthodontics; 24(6); pp. 360-367; (Author Manuscript); Jun. 1990.
Chafetz et al., "Subsidence of the Femoral Prosthesis, A Stereophotogrammetric Evaluation", Clinical Orthopaedics and Related Research; No. 201; pp. 60-67; Dec. 1985.
Chiappone, "Constructing the Gnathologic Setup and Positioner", Journal of Clinical Orthodontics; 14(2); pp. 121-133; Feb. 1980.
Siemens; Cerec—"Computer-Reconstruction, High Tech in der Zahnmedizin", 15 pages; (Includes Machine Translation); (year of pub. sufficiently earlier than effective US filing date and any foreign priority date); 2004.
Sinclair, "The Readers' Corner", Journal of Clinical Orthodontics; 26(6); pp. 369-372; 5 pages; retrived from the internet (http://www.jco-online.comlarchive/print_article .asp?Year= 1992&Month=06 &ArticleNum=); Jun. 1992.
Stoll et al.; "Computer-aided Technologies in Dentistry", Dtsch Zahna'rztl Z 45, pp. 314-322; (English Abstract Included); (year of pub. sufficiently earlier than effective US filing date and any foreign priority date) 1990.
Sturman, "Interactive Keyframe Animation of 3-D Articulated Models", Proceedings Graphics Interface '84; vol. 86; pp. 35-40; May-Jun. 1984.
The American Heritage, Stedman's Medical Dictionary; "Gingiva"; 3 pages; retrieved from the interent (http://reference.com/search/search?q=gingiva) on Nov. 5, 2004.
The Dental Company Sirona, "Cerec Omnicam and Cerec Bluecam. The first choice in every case", product brochure, 8 pages; (year of pub. sufficiently earlier than effective US filing date and any foreign priority date) 2014.
Thera Mon; "Microsensor"; "2 pages"; retrieved from the internet (www.english.thera-mon.com/the-product/transponder/index.html); on Sep. 19, 2016.
Thorlabs; Pellin broca prisms; 1 page; retrieved from the internet (www.thorlabs.com); Nov. 30, 2012.
Truax, "Truax Clasp-Less(TM) Appliance System", The Functional Orthodontist; 9(5); pp. 22-24, 26-28; Sep.-Oct. 1992.
Tru-Tatn Orthodontic & Dental Supplies, Product Brochure, Rochester, Minnesota 55902, 16 pages; (year of pub. sufficiently earlier than effective US filing date and any foreign priority date) 1996.

U.S. Department of Commerce, National Technical Information Service, "Holodontography: An Introduction to Dental Laser Holography", School of Aerospace Medicine Brooks AFB Tex; Mar. 1973, 37 pages.
Schmidt, et al. "Automated Crown Replication Using Solid Photography SM", National Technical Information Service, Solid Photography Inc., Melville NY,; Oct. 1977; 19 pages.
Van Der Linden, "A New Method to Determine Tooth Positions and Dental Arch Dimensions", Journal fo Dental Research; 51(4); p. 1104; Jul.-Aug. 1972.
Van Der Linden et al, "Three-Dimensional Analysis of Dental Casts by Means of the Optocom", Journal of Dental Research; 51 (4 ); p. 11 00; Jul.-Aug. 1972.
Van Der Zel, "Ceramic-Fused-to-Metal Restorations with a New CAD/Cam System", Quintessence International; 24 (A); pp. 769-778; (year of pub. Sufficiently earlier than effective US filing date and any foreign priority date); 1993.
Van Hilsen et al., "Comparing potential early caries assessment methods for teledentistry", BMC Oral Health; 13(16); doi: 101186/1472-6831-13-16; 9 pages; Mar. 2013.
Varady et al.; "Reverse Engineering of Geometric Models—An Introduction", Computer-Aided Design; 29(4 ); pp. 255-268; 29 pages; (Author Manuscript); May 13, 1996.
Verstreken et al., "An Image-Guided Planning System for Endosseous Oral Implants", IEEE Transactions on Medical Imaging; 17(5); pp. 842-852; Oct. 1998.
Warunek et al., "Physical and Mechanical Properties of Elastomers in Orthodonic Positioners", American Journal of Orthodontics and Dentofacial Orthopedics; 95(5); pp. 388-400; 21 pages; (Author Manuscript); May 1989.
Warunek et.al., "Clinical Use of Silicone Elastomer Applicances", JCO; 23 (10); pp. 694-700; Oct. 1989.
Wells, "Application of the Positioner Appliance in Orthodontic Treatment", American Journal of Orthodontics; 58( 4 ); pp. 351-366; Oct. 1970.
Wishan, "New Advances in Personal Computer Applications for Cephalometric Analysis, Growth Prediction, Surgical Treatment Planning and Imaging Processing", Symposium: Computerized Facial Imaging in Oral and Maxilofacial Surgery; p. 5; Presented on Sep. 13, 1990.
Wikipedia; Palatal expansion; 3 pages; retrieved from the internet (https://en.wikipedia.org/wiki/Palatal_expansion) on Mar. 5, 2018.
Williams, "Dentistry and CAD/Cam: Another French Revolution", J. Dent. Practice Admin.; 4(1); pp. 2-5 Jan./Mar. 1987.
Williams, "The Switzerland and Minnesota Developments in CAD/CAM", Journal of Dental Practice Administration; 4(2); pp. 50-55; Apr./Jun. 1987.
Wireless Sensor Networks Magazine, "Embedded Teeth for Oral Activity Recognition", Jul. 29, 2013, 2 pages; retrieved on Sep. 19, 2016 from the internet (www.wsnmagazine.com/embedded-teeth/).
Witt et al., "The wear-timing measuring device in orthodontics—cui bono? Reflections on the state-of-the-art in wear-timing measurement and compliance research in orthodontics"; Fortschr Kieferothop; 52(3); pp. 117-125; (Translation Included) Jun. 1991.
WSCG'98—Conference Program, The Sixth International Conference in Central Europe on Computer Graphics and Visualization '98; pp. 1-7; retrieved from the Internet on Nov. 5, 2004, (http://wscg.zcu.cz/wscg98/wscg98.htm); Feb. 9-13, 1998.
Xia et al., "Three-Dimensional Virtual-Reality Surgical Planning and Soft-Tissue Prediction for Orthognathic Surgery", IEEE Transactions on Information Technology in Biomedicine; 5(2); pp. 97-107; Jun. 2001.
Yamada et al., "Simulation of fan-beam type optical computer-tomography imaging of strongly scattering and weakly absorbing media", Applied Optics; 32(25); pp. 4808-4814; Sep. 1, 1993.
Yamamoto et al., "Optical Measurement of Dental Cast Profile and Application to Analysis of Three-Dimensional Tooth Movement in Orthodontics", Front. Med. Biol. Eng., 1(2); pp. 119-130; (year of pub. sufficiently earlier than effective US filing date and any foreign priority date); 1988.
Yamamoto et al., "Three-Dimensional Measurement of Dental Cast Profiles and Its Applications to Orthodontics", Conf. Proc. IEEE Eng. Med. Bioi. Soc.; 12(5); pp. 2052-2053; Nov. 1990.

(56) References Cited

OTHER PUBLICATIONS

Yamany et al., "A System for Human Jaw Modeling Using Intra-Oral Images", Proc. of the 20th Annual Conf. of the IEEE Engineering in Medicine and Biology Society; vol. 2; pp. 563-566; Oct. 1998.
Yoshii, "Research on a New Orthodontic Appliance: The Dynamic Positioner (D.P.); I. The D.P. Concept and Implementation of Transparent Silicone Resin (Orthocon)"; Nippon Dental Review; 452; pp. 61-74; 32 pages; (Author Manuscript); Jun. 1980.
Yoshii, "Research on a New Orthodontic Appliance: The Dynamic Positioner (D.P.); II. The D.P. Manufacturing Procedure and Clinical Applications", Nippon Dental Review; 454; pp. 107-130; 48 pages; (Author Manuscript); Aug. 1980.
Yoshii, "Research on a New Orthodontic Appliance: The Dynamic Positioner (D.P.)—III. The General Concept of the D.P. Method and Its Therapeutic Effect, Part 1, Dental and Functional Reversed Occlusion Case Reports", Nippon Dental Review; 457; pp. 146-164; 43 pages; (Author Manuscript); Nov. 1980.
Yoshii, "Research on a New Orthodontic Appliance: The Dynamic Positioner (D.P.); III—The General Concept of the D.P. Method and Its Therapeutic Effect, Part 2. Skeletal Reversed Occlusion Case Reports", Nippon Dental Review; 458; pp. 112-129; 40 pages; (Author Manuscript); Dec. 1980.
Japanese Patent Office, Office Action for Japanese Patent Application No. JP 2017-500896 dated Dec. 18, 2018.
Park, H. et al. "Development of High Speed and High Accuracy 3D Dental Intra Oral Scanner," Procedia Eng. 100 (2015) 1174-1181.
Third-Party Submission Under 37 CFR 1.290 for U.S. Appl. No. 15/859,010, filed Jan. 11, 2019.
International Search Report and Written Opinion for PCT Application No. PCT/IB2015/001400 dated Feb. 9, 2016, 18 pages.
Tiziani H. J. et al., "Confocal principle for macro- and microscopic surface and defect analysis," Optical Engineering, Jan. 1, 2000, pp. 32-39, vol. 39(1), Society of Photo-Optical Instrumentation Engineers.
Chishti et al.; U.S. Appl. No. 60/050,342 entitled "Procedure for Moving Teeth Using a Seires of Retainers," filed Jun. 20, 1997.
Cottingham, "Gnathologic Clear Plastic Positioner", American Journal of Orthodontics; 55(1 ); pp. 23-31; Jan. 1969.
Crawford; CAD/CAM in the Dental Office: Does It Work?; Canadian Dental Journal; 57(2); pp. 121-123 Feb. 1991.
Crawford, Computers in Dentistry: Part 1: CAD/CAM: The Computer Moves Chairside, Part 2: F. Duret—A Man With a Vision, Part 3: The Computer Gives New Vision—Literally, Part 4: Bytes 'N Bites The Computer Moves From The Front Desk to The Operatory; Canadian Dental Journal; 54(9); pp. 661-666 Sep. 1988.
Crooks; CAD/CAM Comes to USC; USC Dentistry; pp. 14-17; (year of pub. sufficiently earlier than effective US filing date and any foreign priority date) Spring 1990.
Cureton, "Correcting Malaligned Mandibular Incisors with Removable Retainers", Journal of Clinical Orthodontics; 30(7); pp. 390-395; Jul. 1996.
Curry et al., "Integrated Three-Dimensional Craniofacial Mapping at the Craniofacial Research Instrumentation Laboratory / University of the Pacific", Seminars in Orthodontics; 7(4 ); pp. 258-265; Dec. 2001.
Cutting et al., "Three-Dimensional Computer-Assisted Design of Craniofacial Surgical Procedures: Optimization and Interaction with Cephalometric and CT-Based Models", Plastic and Reconstructive Surgery; 77(6); pp. 877-885; Jun. 1986.
DCS Dental AG; The CAD/CAM 'DCS Titan System' for Production of Crowns/Bridges; DSC Production; pp. 1-7; Jan. 1992.
Defranco et al., "Three-Dimensional Large Displacement Analysis of Orthodontic Appliances", Journal of Biomechanics; 9( 12); pp. 793-801; Jan. 1976.
Dental Institute University of Zurich Switzerland; Program for International Symposium on Computer Restorations: State of the Art of the CEREC-Method; 2 pages; May 1991.
Dentrac Corporation; Dentrac document; pp. 4-13; (year of pub. sufficiently earlier than effective US filing date and any foreign priority date) 1992.
Dent-X; "DentSim . . . Dent-x's virtual reality 3-D training simulator . . . A revolution in dental education", 6 pages; retrieved from the internet (http://www.dent-x.com/DentSim.htm); on Sep. 24, 1998.
Doruk et al., "The role of the headgear timer in extraoral co-operation", European Journal of Orthodontics; 26; pp. 289-291; Jun. 1, 2014.
Doyle; "Digital Dentistry, Doctors use CAD/CAM to take the pain out of extensive dental procedures", Computer Graphics World; pp. 50-52 and p. 54; Oct. 2000.
Dummer et al., "Computed Radiography Imaging Based on High-Density 670 nm VCSEL Arrays", International Society for Optics and Photonics; vol. 7557, p. 75570H, 7 pages; (Author Manuscript); Feb. 24, 2010.
Duret et al., "CAD/CAM Imaging in Dentistry", Current Opinion in Dentistry; 1 (2); pp. 150-154; Apr. 1991.
Duret et al; CAD-CAM in Dentistry; Journal of the American Dental Association; 117(6); pp. 715-720; Nov. 1988.
Duret, "The Dental CAD/CAM, General Description of the Project", Hennson International Product Brochure, 18 pages; Jan. 1986.
Duret; Vers Une Prosthese Informatisee; Tonus; 75(15); pp. 55-57; (English translation attached); 23 pages; Nov. 15, 1985.
Economides, "The Microcomputer in the Orthodontic Office", Journal of Clinical Orthodontics; 13(11); pp. 767-772; Nov. 1979.
Elsasser, "Some Observations on the History and Uses of the Kesling Positioner", American Journal of Orthodontics; 36(5); pp. 368-374; May 1, 1950.
Faber et al., "Computerized Interactive Orthodontic Treatment Planning", American Journal of Orthodontics; 73(1 ); pp. 36-46; Jan. 1978.
Felton et al., "A Computerized Analysis of the Shape and Stability of Mandibular Arch Form", American Journal of Orthodontics and Detofacial Orthopedics, Dec. 1987, pp. 478-483, vol. 92 No. 6, The C. V. Mosby Company.
Friede et al., "Accuracy of Cephalometric Prediction in Orthognathic Surgery", Journal of Oral and Maxillofacial Surgery; 45(9); pp. 754-760; Sep. 1987.
Friedrich et al; "Measuring system for in vivo recording of force systems in orthodontic treatment-concept and analysis of accuracy", J. Biomech.; 32(1); pp. 81-85; (Abstract only) Jan. 1999.
Futterling et al, "Automated Finite Element Modeling of a Human Mandible with Dental Implants", JS WSCG '98—Conference Program; 8 pages; retrieved from the Internet (https://dspace5.zcu.cz/bitstream/11025/15851/1/Strasser_98.pdf); on Aug. 21, 2018.
Gao et al., "3-D Element Generation for Multi-Connected Complex Dental and Mandibular Structure", IEEE Proceedings International Workshop in Medical Imaging and Augmented Reality; pp. 267-271; Jun. 12, 2001.
Gim-Alldent Deutschland, "Das DUX System: Die Technik," 3 pages; (English Translation Included}; (year of pub. sufficiently earlier than effective US filing date and any foreign priority date); 2002.
Gottleib et al., JCO Interviews Dr. James A. McNamura, Jr., on the Frankel Appliance: Part 2: Clinical Management:, Journal of Clinical Orthodontics; 16(6), Jun. 1982, pp. 390-407; retrieved from the internet (http://www.jco-online.com/archive/print_article.asp?Year=1982&Month=06&ArticleNum+) on Mar. 9, 2005.
Grayson, "New Methods for Three Dimensional Analysis of Craniofacial Deformity", Symposium: Computerized Facial Imaging in Oral and Maxillofacial Surgery; American Association of Oral and Maxillofacial Surgeons; 48(8) suppl 1; pp. 5-6; Sep. 13, 1990.
Grest, Daniel, Marker-Free Human Motion Capture in Dynamic Cluttered Environments from a Single View-Point:, PhD Thesis; 167 pages; Dec. 2007, Kiel, Germany.
Guess et al. "Computer Treatment Estimates in Orthodontics and Orthognathic Surgery" Journal of Clinical Orthodontics; 23(4); pp. 262-268; 11 pages; (Author Manuscript); Apr. 1989.

(56) References Cited

OTHER PUBLICATIONS

Heaven et al.; Computer-Based Image Analysis of Artificial Root Surface Caries; Abstracts of Papers #2094; Journal of Dental Research; vol. 70, Special Issue; p. 528; (Abstract Only); Apr. 17-21, 1991.

Highbeam Research, "Simulating stress put on jaw. (ANSYS Inc.'s finite element analysis software)" Nov. 1, 1996, 2 pages; retrieved from the Internet (http://static.highbeam.eom/titoolingampproduction/november011996/simulatingstressputonfa . . . ); on Nov. 5, 2004.

Hikage, "Integrated Orthodontic Management System for Virtual Three-Dimensional Computer Graphic Simulation and Optical Video Image Database for Diagnosis and Treatment Planning" Journal of Japan KA Orthodontic Society; 46(2); pp. 248-269; 56 pages; (English Translation Included); Feb. 26, 1987.

Hoffmann et al., "Role of Cephalometry for Planning of Jaw Orthopedics and Jaw Surgery Procedures", Informatbnen, pp. 375-396; (English Abstract Included); Mar. 1991.

Hojjatie et al., Three-Dimensional Finite Element Analysis of Glass-Ceramic Dental Crowns; Journal of Biomechanics; 23(11); pp. 1157-1166; Jan. 1990.

Huckins, "CAD-CAM Generated Mandibular Model Prototype from MRI Data", AAOMS, p. 96; (Abstract Only); (year of pub. sufficiently earlier than effective US filing date and any foreign priority date) 1999.

Invisalign; "You were made to move. There's never been a better time to straighten your teeth with the most advanced clear aligner in the world"; Product webpage; 2 pages; retrieved from the internet (www.invisalign.com/) on Dec. 28, 2017.

JCO Interviews, "Craig Andreiko , DDS, MS on the Elan and Orthos Systems; Interview by Dr. Larry W. White", Journal of Clinical Orthodontics; 28(8); pp. 459-468; 14 pages; (Author Manuscript); Aug. 1994.

JCO Interviews; "Dr. Horner W. Phillips on Computers in Orthodontic Practice, Part 2", Journal of Clinical Orthodontics; 17(12); pp. 819-831; 19 pages; Dec. 1983.

Jerrold, "The Problem, Electronic Data Transmission and the Law", American Journal of Orthodontics and Dentofacial Orthopedics; 113(4 ); 5 pages; (Author Manuscript); Apr. 1998.

Jones et al.; An Assessment of the Fit of a Parabolic Curve to Pre- and Post-Treatment Dental Arches; British Journal of Orthodontics; 16(2); pp. 85-93; May 1989.

Kamada et al., "Case reports on Tooth Positioners Using LTV Vinyl Silicone Rubber", J. Nihon University School of Dentistry; 26(1); pp. 11-29; (year of pub. Sufficiently earlier than effective US filing date and any foreign priority date) 1984.

Kamada et al. "Construction of Tooth Positioners with OTV Vinyl Silicone Rubber and Some Case Reports", J. Nihon University School of Dentistry; 24(1); pp. 1-27; (year of pub. Sufficiently earlier than effective US filing date anda ny foreign priority date) 1982.

Kanazawa et al., "Three-Dimensional Measurements of the Occlusal Surfaces of Upper Molars in a Dutch Population", Journal of Dental Research; 63(11); pp. 1298-1301; Nov. 1984.

Kesling et al., "The Philosophy of the Tooth Positioning Appliance", American Journal of Orthodontics and Oral Surgery; 31 (6); pp. 297-304; Jun. 1945.

Kesling, "Coordinating the Predetermined Pattern and Tooth Positioner with Conventional Treatment", American Journal of Orthodontics and Oral Surgery; 32(5); pp. 285-293; May 1946.

Office Action for Chinese Patent Application No. 201580056255.2 dated Jan. 16, 2019,Chinese only, 7 pages.

Office Action for Chinese Patent Application No. 201580037043.X dated Jan. 2, 2019, with English translation, 18 pages.

Second Office Action for Chinese Patent Application No. 201580037043.X dated Jun. 19, 2019, with English translation, 22 pages.

Japanese Patent Office, Office Action for Japanese Patent Application No. JP 2017-500896 dated Jun. 11, 2019, with English translation, 6 pages.

* cited by examiner

IMAGING APPARATUS WITH SIMPLIFIED OPTICAL DESIGN

RELATED APPLICATIONS

This patent application is a continuation application of U.S. patent application Ser. No. 15/610,515, filed May 31, 2017, which is a divisional application of U.S. patent application Ser. No. 14/825,173, filed Aug. 13, 2015, which claims the benefit under 35 U.S.C. § 119(e) of U.S. Provisional Application No. 62/037,778, filed Aug. 15, 2014, all of which are herein incorporated by reference.

TECHNICAL FIELD

Embodiments of the present invention relate to the field of imaging and, in particular, to a system and method for performing confocal imaging of a three dimensional surface.

BACKGROUND

A great variety of methods and systems have been developed for direct optical measurement of teeth and the subsequent automatic manufacture of dentures. The term "direct optical measurement" signifies surveying of teeth in the oral cavity of a patient. This facilitates the obtainment of digital constructional data necessary for the computer-assisted design (CAD) or computer-assisted manufacture (CAM) of tooth replacements without having to make any cast impressions of the teeth. Such systems typically include an optical probe coupled to an optical pick-up or receiver such as charge coupled device (CCD) or complementary meta-oxide semiconductor (CMOS) sensor and a processor implementing a suitable image processing technique to design and fabricate virtually the desired product.

One type of system that performs intra-oral scans is a system that uses confocal imaging to image a three dimensional surface. Such systems that use confocal imaging typically include field lenses to flatten an imaging field and enable flat focal planes for emitted light beams. Such flat focal planes ensure that the surface topology of scanned three dimensional surfaces is accurate. However, the field lenses are diverging lenses that open the rays of the light beams. This causes the optics of the confocal imaging apparatus to be enlarged. Additionally, the field lenses should be aligned to ensure accuracy. Such alignment can be a time consuming and challenging process.

BRIEF DESCRIPTION OF THE DRAWINGS

The present invention is illustrated by way of example, and not by way of limitation, in the figures of the accompanying drawings.

DETAILED DESCRIPTION

Described herein is a confocal imaging apparatus having a non-flat focal surface. The non-flat focal surface may be caused by the optics of the confocal imaging apparatus lacking a field lens. As is discussed in greater detail below, the lack of a field lens in the confocal imaging apparatus introduces challenges but also provides numerous advantages. For example, a confocal imaging apparatus without a field lens is smaller, lighter and easier to manufacture than a confocal imaging apparatus having a field lens. Embodiments discussed herein show how to overcome the challenges in designing and using a confocal imaging apparatus lacking a field lens.

Also described herein is a large field confocal imaging apparatus having focusing optics that change a magnification of a focal surface with changes in a focusing setting. As is discussed in greater detail below, the change in magnification introduces challenges that are overcome in embodiments.

In one embodiment, a confocal imaging apparatus includes an illumination module to generate an array of light beams. Focusing optics of the confocal imaging apparatus perform confocal focusing of an array of light beams onto a non-flat focal surface and direct the array of light beams toward a three dimensional object to be imaged. A translation mechanism of the confocal imaging apparatus adjusts a location of at least one lens to displace the non-flat focal surface along an imaging axis. A detector of the confocal imaging apparatus measures intensities of an array of returning light beams that are reflected off of the three dimensional object and directed back through the focusing optics. Intensities of the array of returning light beams are measured for locations of the at least one lens for determination of positions on the imaging axis of points of the three dimensional object. Detected positions of one or more points are adjusted to compensate for the non-flat focal surface. Thus, an object may be accurately imaged despite the non-flat focal surface of the confocal imaging apparatus.

Figure 1A:
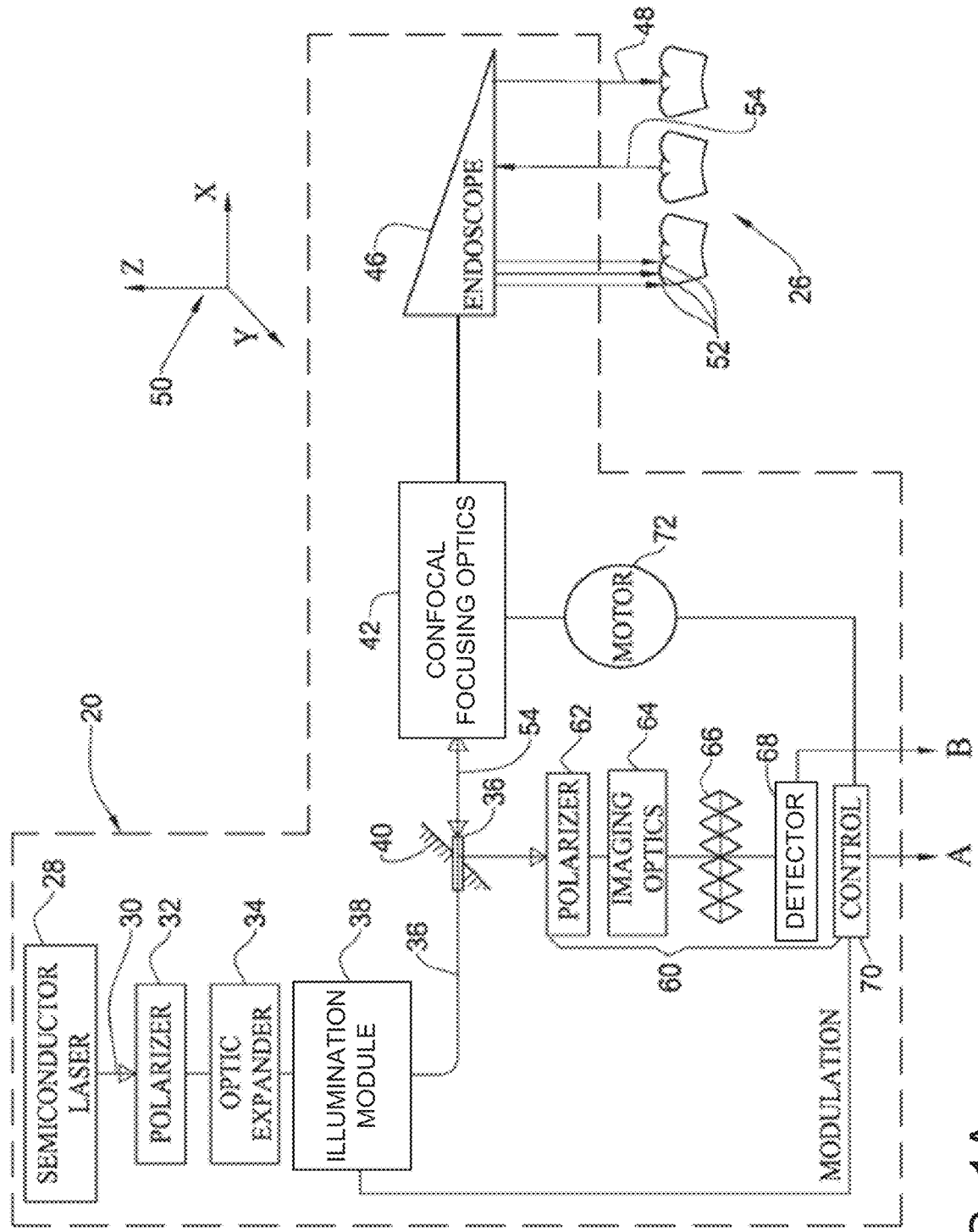
FIG. 1A illustrates a functional block diagram of a confocal imaging apparatus according to one embodiment.
Figure 1B:
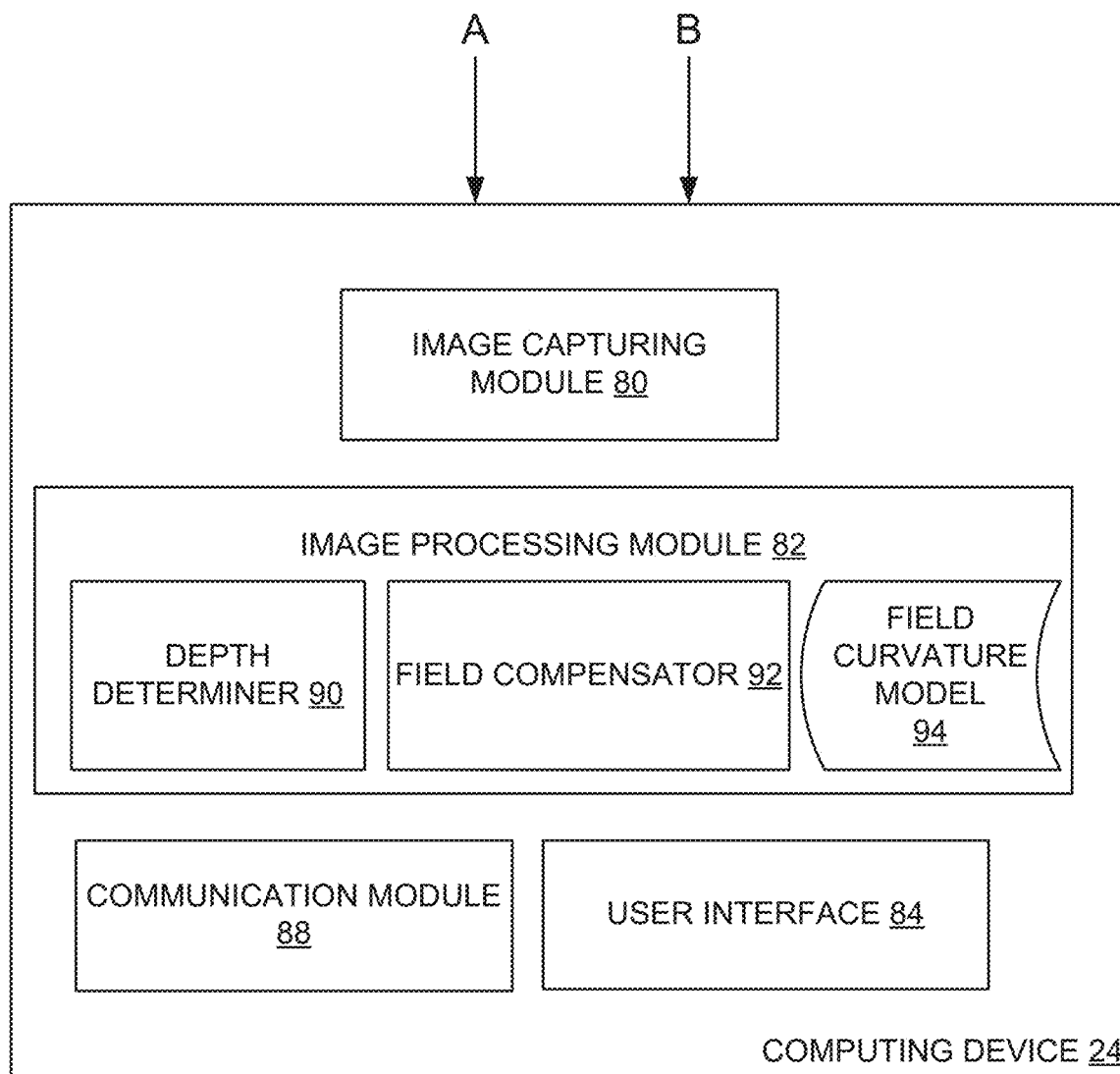
FIG. 1B illustrates a block diagram of a computing device that connects to a confocal imaging apparatus, in accordance with one embodiment.

FIG. 1A illustrates a functional block diagram of a confocal imaging apparatus 20 according to one embodiment. FIG. 1B illustrates a block diagram of a computing device 24 that connects to the confocal imaging apparatus 20. Together, the confocal imaging apparatus 20 and computing device 24 may form a system for generating three dimensional images of scanned objects. The computing device 24 may be connected to the confocal imaging apparatus 20 directly or indirectly and via a wired or wireless connection. For example, the confocal imaging apparatus 20 may include a network interface controller (NIC) capable of communicating via Wi-Fi, via third generation (3G) or fourth generation (4G) telecommunications protocols (e.g., global system for mobile communications (GSM), long term evolution (LTE), Wi-Max, code division multiple access (CDMA), etc.), via Bluetooth, via Zigbee, or via other wireless protocols. Alternatively, or additionally, confocal imaging apparatus may include an Ethernet network interface controller (NIC), a universal serial bus (USB) port, or other wired port. The NIC or port may connect the confocal imaging apparatus to the computing device via a local area network (LAN). Alternatively, the confocal imaging apparatus 20 may connect to a wide area network (WAN) such as the Internet, and may connect to the computing device 24 via the WAN. In an alternative embodiment, confocal imaging apparatus 20 is connected directly to the computing device (e.g., via a direct wired or wireless connection). In one embodiment, the computing device 24 is a component of the confocal imaging apparatus 20.

Referring now to FIG. 1A, in one embodiment confocal imaging apparatus 20 includes a semiconductor laser unit 28 that emits a focused light beam, as represented by arrow 30. The light beam 30 passes through a polarizer 32. Polarizer 32 polarizes the light beam passing through polarizer 32. Alternatively, polarizer 32 may be omitted in some embodiments. The light beam then enters into an optic expander 34 that improves a numerical aperture of the light beam 30. The light beam 30 then passes through an illumination module 38, which splits the light beam 30 into an array of incident light beams 36, represented here, for ease of illustration, by a single line. The illumination module 38 may be, for example, a grating or a micro lens array that splits the light beam 30 into an array of light beams 36. In one embodiment, the array of light beams 36 is an array of telecentric light beams. Alternatively, the array of light beams may not be telecentric.

The confocal imaging apparatus 20 further includes a unidirectional mirror or beam splitter (e.g., a polarizing beam splitter) 40 that passes the array of light beams 36. A unidirectional mirror 40 allows transfer of light from the semiconductor laser 28 through to downstream optics, but reflects light travelling in the opposite direction. A polarizing beam splitter allows transfer of light beams having a particular polarization and reflects light beams having a different (e.g., opposite) polarization. In one embodiment, the unidirectional mirror or beam splitter 40 has a small central aperture. The small central aperture may improve a measurement accuracy of the confocal imaging apparatus 20. In one embodiment, as a result of a structure of the unidirectional mirror or beam splitter 40, the array of light beams will yield a light annulus on an illuminated area of an imaged object as long as the area is not in focus. Moreover, the annulus will become a completely illuminated spot once in focus. This ensures that a difference between measured intensities of out-of focus points and in-focus points will be larger.

Along an optical path of the array of light beams after the unidirectional mirror or beam splitter 40 are confocal focusing optics 42, and an endoscopic probing member 46. Additionally, a quarter wave plate may be disposed along the optical path after the unidirectional mirror or beam splitter 40 to introduce a certain polarization to the array of light beams. In some embodiments this may ensure that reflected light beams will not be passed through the unidirectional mirror or beam splitter 40. Confocal focusing optics 42 may additionally include relay optics (not shown). Confocal focusing optics 42 may or may not maintain the same magnification of an image over a wide range of distances in the Z direction, wherein the Z direction is a direction of beam propagation (e.g., the Z direction corresponds to an imaging axis that is aligned with an optical path of the array of light beams 36). The relay optics enable the confocal imaging apparatus 20 to maintain a certain numerical aperture for propagation of the array of light beams 36. The confocal focusing optics 42 and endoscopic probing member 46 are discussed in greater detail with reference to FIGS. 2A-2C.

The endoscopic probing member 46 may include a rigid, light-transmitting medium, which may be a hollow object defining within it a light transmission path or an object made of a light transmitting material, e.g. a glass body or tube. In one embodiment, the endoscopic probing member 46 include a prism such as a folding prism. At its end, the endoscopic probing member 46 may include a mirror of the kind ensuring a total internal reflection. Thus, the mirror may direct the array of light beams towards a teeth segment 26 or other object. The endoscope probing member 46 thus emits array of light beams 48, which impinge on to surfaces of the teeth section 26.

The array of light beams 48 are arranged in an X-Y plane, in the Cartesian frame 50, propagating along the Z axis. As the surface on which the incident light beams hits is an uneven surface, illuminated spots 52 are displaced from one another along the Z axis, at different ($X_i$, $Y_i$) locations. Thus, while a spot at one location may be in focus of the confocal focusing optics 42, spots at other locations may be out-of-focus. Therefore, the light intensity of returned light beams of the focused spots will be at its peak, while the light intensity at other spots will be off peak. Thus, for each illuminated spot, multiple measurements of light intensity are made at different positions along the Z-axis. For each of such ($X_i$, $Y_i$) location, the derivative of the intensity over distance (Z) may be made, with the $Z_i$ yielding maximum derivative, $Z_0$, being the in-focus distance. As pointed out above, the incident light from the array of light beams 48 forms a light disk on the surface when out of focus and a complete light spot when in focus. Thus, the distance derivative will be larger when approaching in-focus position, increasing accuracy of the measurement.

The light scattered from each of the light spots includes a beam travelling initially in the Z axis along the opposite direction of the optical path traveled by the array of light beams 48. Each returned light beam in an array of returning light beams 54 corresponds to one of the incident light beams in array of light beams 36. Given the asymmetrical properties of unidirectional mirror or beam splitter 40, the returned light beams are reflected in the direction of detection optics 60.

The detection optics 60 may include a polarizer 62 that has a plane of preferred polarization oriented normal to the plane polarization of polarizer 32. Alternatively, polarizer 32 and polarizer 62 may be omitted in some embodiments. The array of returning light beams 54 may pass through imaging optics 64 in one embodiment. The imaging optics 64 may be one or more lenses. Alternatively, the detection optics 60 may not include imaging optics 64. In one embodiment, the array of returning light beams 54 further passes through a matrix 66, which may be an array of pinholes. Alternatively, no matrix 66 is used in some embodiments. The array of returning light beams 54 are then directed onto a detector 68.

The detector 68 is an image sensor having a matrix of sensing elements each representing a pixel of the image. If matrix 66 is used, then each pixel further corresponds to one pinhole of matrix 66. In one embodiment, the detector is a charge coupled device (CCD) sensor. In one embodiment, the detector is a complementary metal-oxide semiconductor (CMOS) type image sensor. Other types of image sensors may also be used for detector 68. The detector 68 detects light intensity at each pixel.

In one embodiment, detector 68 provides data to computing device 24. Thus, each light intensity measured in each of the sensing elements of the detector 68, is then captured and analyzed, in a manner to be described below, by processor 24.

Confocal imaging apparatus 20 further includes a control module 70 connected both to semiconductor laser 28 and a motor 72, voice coil or other translation mechanism. In one embodiment, control module 70 is or includes a field programmable gate array (FPGA) configured to perform control operations. Motor 72 is linked to confocal focusing optics 42 for changing a focusing setting of confocal focusing optics 42. This may adjust the relative location of an imaginary non-flat focal surface of confocal focusing optics 42 along the Z-axis (e.g., in the imaging axis). Control module 70 may induce motor 72 to axially displace (change a location of) one or more lenses of the confocal focusing optics 42 to change the focal depth of the imaginary non-flat focal surface. In one embodiment, motor 72 or confocal imaging apparatus 20 includes an encoder (not shown) that accurately measures a position of one or more lenses of the confocal focusing optics 42. The encoder may include a sensor paired to a scale that encodes a linear position. The encoder may output a linear position of the one or more lenses of the confocal focusing optics 42. The encoder may be an optical encoder, a magnetic encoder, an inductive encoder, a capacitive encoder, an eddy current encoder, and so on. After receipt of feedback that the location of the one or more lenses has changed, control module 70 may induce laser 28 to generate a light pulse. Control unit 70 may additionally synchronize image-capturing module 80 from FIG. 1B to receive and/or store data representative of the light intensity from each of the sensing elements at the particular location of the one or more lenses (and thus of the focal depth of the imaginary non-flat focal surface). In subsequent sequences, the location of the one or more lenses (and thus the focal depth) will change in the same manner and the data capturing will continue over a wide focal range of confocal focusing optics 42.

Referring now to FIG. 1B, image capturing module 80 may capture images responsive to receiving image capture commands from the control unit 70. The captured images may be associated with a particular focusing setting (e.g., a particular location of one or more lenses in the confocal focusing optics as output by the encoder). Image processing module 82 then processes captured images captured over multiple different focusing settings. Image processing module 82 includes a depth determiner 90 and a field compensator 92 for processing image data.

Depth determiner 90 determines the relative intensity in each pixel over the entire range of focal settings of confocal focusing optics 42 from received image data. Once a certain light spot associated with a particular pixel is in focus, the measured intensity will be maximal for that pixel. Thus, by determining the corresponding to the maximal light intensity or by determining the maximum displacement derivative of the light intensity, for each pixel, the relative position of each light spot along the Z axis can be determined for each pixel. Thus, data representative of the three-dimensional pattern of a surface in the teeth segment 26 or other three dimensional object can be obtained.

In embodiments, the confocal focusing optics 42 of confocal imaging apparatus 20 lack field lenses. The purpose of the field lens is to flatten a focal field and thus produce a flat focal plane for the array of light beams. For confocal imaging apparatuses with field lenses, each light beam from the array of light beams focuses on the same flat focal plane. However, without such field lenses the array of light beams focus on an imaginary non-flat focal surface (e.g., on a curved focal surface). This causes the Z axis information that depth determiner 90 computes to be distorted for many pixels.

Field compensator 92 compensates for the curved field caused by the lack of a field lens. Field compensator 92 may also compensate for changes in a position of the curved focal surface caused by temperature and/or for magnification changes caused by changes in a focusing setting. Field compensator 92 applies a field curvature model 94 and/or other optics compensation model (not shown) to each Z axis measurement of each pixel to correct for field curvature, temperature and/or magnification changes. In one embodiment, a different field curvature model 94 (or other optics compensation model) is applied for each focusing setting of the confocal imaging apparatus 20. This is because the amount of field curvature and/or magnification may change with changes in the focusing setting. Alternatively, a single field curvature model 94 (or other optics compensation model) may account for the changes in the field curvature caused by changes in the focusing setting and/or for changes in magnification caused by changes in the focusing setting. For each combination of an X,Y pixel location and a focusing setting (e.g., a z-axis position of one or more lenses of the focusing optics), a particular depth adjustment may be applied based on the field curvature model or models. Additionally, an X location adjustment and/or a Y location adjustment bay be applied based on the field curvature model and/or other optics compensation model. In one embodiment, for each combination of an X,Y pixel location, a focusing setting, and a temperature reading or a z-axis position of a measured element whose position changes with changes in temperature, a particular depth adjustment may be applied based on the field curvature model or models. The adjusted depth (z-axis) values represent the actual z-axis values of the imaged surface.

A three-dimensional representation may be constructed based on the corrected measurement data and displayed via a user interface 84. The user interface 84 may be a graphical user interface that includes controls for manipulating a display of the three-dimensional representation (e.g., viewing from different angles, zooming-in or out, etc.). In addition, data representative of the surface topology of the scanned object may be transmitted to remote devices by a communication module 88 for further processing or use (e.g., to generate a three dimensional virtual model of the scanned object).

By capturing, in this manner, an image from two or more angular locations around the structure, e.g. in the case of a teeth segment from the buccal direction, from the lingual direction and optionally from above the teeth, an accurate three-dimensional representation of the teeth segment may be reconstructed. This may allow a virtual reconstruction of the three-dimensional structure in a computerized environment or a physical reconstruction in a CAD/CAM apparatus. For example, a particular application is imaging of a segment of teeth having at least one missing tooth or a portion of a tooth. In such an instance, the image can then be used for the design and subsequent manufacture of a crown or any other prosthesis to be fitted into this teeth segment.

Figure 2A:
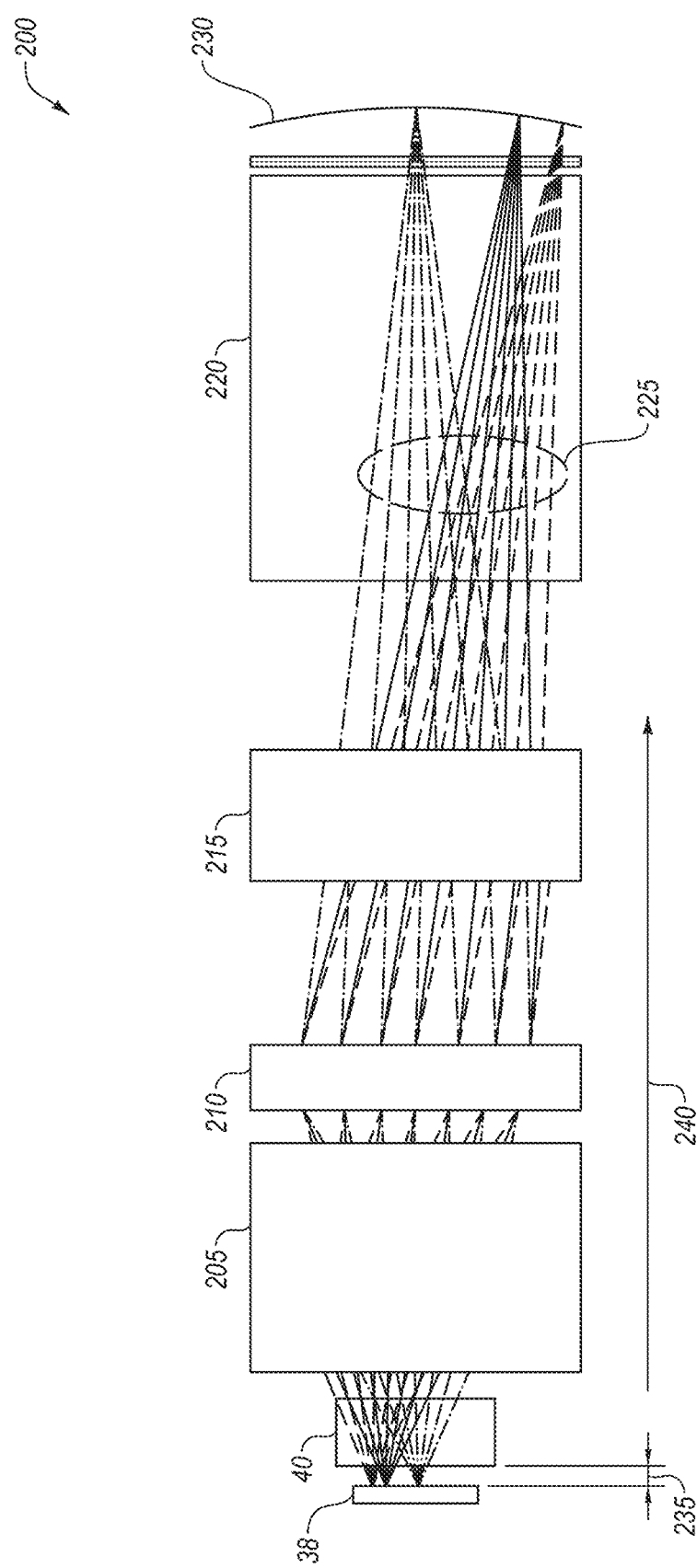
FIG. 2A illustrates optics of a confocal imaging apparatus that lacks a field lens, in accordance with one embodiment.

FIG. 2A illustrates optics 200 of a confocal imaging apparatus that lacks a field lens, in accordance with one embodiment. The optics 200 may correspond to optics of confocal imaging apparatus 20 of FIG. 1A, such as confocal focusing optics 42.

The optics 200 include an illumination module 38, a unidirectional mirror or beam splitter 40, a series of lenses that may correspond to confocal focusing optics 42, and folding prism 220 arranged along an optical path traversed by an array of light beams 225. The optical path is shown to be a linear path. However, in embodiments one or more of the components of optics 200 may change a direction of the optical path. For example, the folding prism 220 may include a mirror (not shown) that may reflect light beams at an angle. An example of such a folding prism is shown in FIG. 3B. Referring back to FIG. 2, an imaging axis 240 is shown that is aligned to the optical path traversed by the array of light beams 225. The imaging axis 240 is a Z-axis that represents depth. As used herein, the imaging axis (or Z axis) may be a curvilinear coordinate axis that corresponds to the optical path. Thus, if the optical path changes direction, the imaging axis changes direction correspondingly.

Illumination module 38 is a source of multiple light beams. In one embodiment, illumination module is a micro lens array that divides an incoming light beam into array of light beams 225. In one embodiment, the array of light beams output by the illumination module 38 is an array of telecentric light beams. Accordingly, chief rays of the array of light beams may be parallel to each other. Unidirectional mirror or beam splitter 40 is disposed along the optical path of the array of light beams, and passes the array of light beams received from the unidirectional mirror or beam splitter 40.

In one embodiment, the confocal focusing optics are divided into a series of lens groups including a first lens group 205, a second lens group 215 and a third lens group 210. First and/or second lens groups 205, 215 may act as relay optics. The first and second lens groups 205, 215 are configured to focus the array of light beams and compensate for optical aberrations. Optical aberrations that may be corrected include shape aberrations, coma, stigmatism, and so forth. In one embodiment, the first and second lens groups 205, 215 are configured to produce an approximately rectangular field having minimal optical distortion. The first lens group 205 and second lens group 215 may have a fixed position relative to each other and to other components of the optics 200. The third lens group 210 has a variable location that may be adjusted to change a location of a curved focal surface produced by the optics 200.

The third lens group 210 is movable along the imaging axis (z axis), but has a fixed position normal to the imaging axis. A focusing setting of the focusing optics can be adjusted by moving the third lens group 210 along the imaging axis. Third lens group 210 may be adjusted to perform scanning of an object. To scan an object, the third lens group 210 may be displaced to numerous different locations (encoder positions) along the imaging axis 240, and images may be taken at each location. In one embodiment, an axial gain of the focusing optics is approximately 7×. Accordingly, a displacement of the third lens group 210 adjusts a location of a curved focal surface 230 by seven times the amount of displacement. For example, a 1 mm displacement of the third lens group 210 causes a position of the curved focal surface (also referred to as a curved focal plane) by 7 mm. This enables the optics 200 to be compact and minimizes movement during operation.

In one embodiment, second lens group 215 focuses the array of light beams 225 into prism 220, which may be a folding prism. Prism 220 may be configured to provide an appropriate refractive index (e.g., that corresponds to a refractive index of glass).

The optics 200 lack any field lens. A field lens is used to flatten a focal surface (flatten an imaging field) to achieve a flat focal plane. As shown, there is no field lens between the illumination module 38 and the unidirectional mirror or beam splitter 40. Nor is there a field lens near prism 220 or a field lens between the unidirectional mirror or beam splitter 40 and a detector (not shown). The lack of a field lens introduces numerous advantages over confocal imaging apparatuses that use field lenses. The field lens is a diverging lens that causes a radius of the lenses used for the focusing optics and/or for relay optics to be larger. This in turn increases the amount of material (e.g., glass) used in the lenses and thus increases a weight of the confocal imaging apparatus. Additionally, the larger lenses cause a thickness of the confocal imaging apparatus to be larger. For example, an example confocal imaging apparatus with a field lens includes a largest lens having a distance from an optical axis to an outer perimeter of the lens of about 15 mm. In contrast, the same confocal imaging apparatus without a field lens may include a largest lens having a distance from the optical axis to an outer perimeter of the lens of less than 15 mm (e.g., less than 13 mm or about 9 mm in embodiments).

In a confocal imaging apparatus having a field lens, the field lens may be positioned between the illumination module 38 and the unidirectional mirror or beam splitter 40. This causes a spacing between the illumination module 38 and the unidirectional mirror or beam splitter 40 to be about 7 mm. Additionally, a corresponding field lens would be placed between the unidirectional mirror or beam splitter 40 and a detector (not shown) at a distance of about 7 mm. In contrast, by eliminating the field lens, the distance 235 between the illumination module 38 and the unidirectional mirror or beam splitter 40 may be less than 7 mm (e.g., less than 5 mm or about 2 mm in embodiments). This further reduces the size of the confocal imaging apparatus.

As mentioned, if a field lens is used in a confocal imaging apparatus, then in actuality two field lenses are used. These two field lenses should be matching field lenses and should be carefully aligned to one another. This alignment can be a time consuming process. Additionally, failure to exactly align these field lenses introduces inaccuracy into the confocal imaging apparatus. Accordingly, an accuracy of the confocal imaging apparatus can be improved and an ease of manufacture for the confocal imaging apparatus can be improved by eliminating the field lens.

The lack of a field lens causes the focal surface 230 to be a curved focal surface (or other non-flat focal surface). The shape of the curved focal surface 230 may depend on the focusing setting of the focusing optics (e.g., the location of the third lens group 210). The curved focal surface may introduce significant error into the confocal imaging apparatus, which accounts for the inclusion of field lenses in prior confocal imaging apparatuses. However, embodiments of the present invention provide a field compensator (see, e.g., field compensator 92 of FIG. 1B) that minimizes or eliminates the error introduced by the lack of a field lens.

As shown, the confocal focusing optics is a non-telecentric optical system. Accordingly, magnification of an imaged object may change with changes in depth and/or in changes of focal settings. However, such magnification changes (and any accompanying distortion) may be accommodated and corrected by the field compensator based on application of a field curvature model. Alternatively, the confocal focusing optics may operate in a telecentric mode, and distance-introduced magnification changes may be avoided.

Figure 2B:
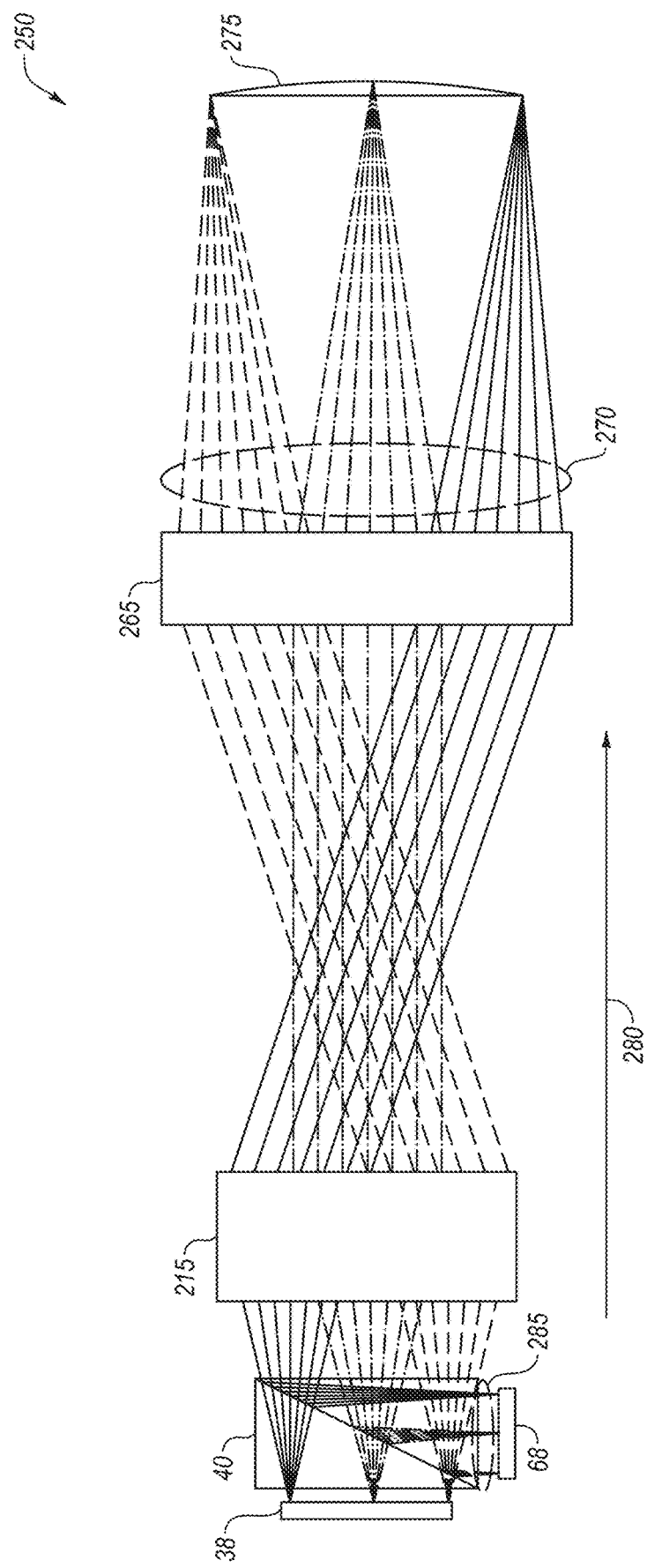
FIG. 2B illustrates optics of a confocal imaging apparatus that lacks a field lens, in accordance with another embodiment.

FIG. 2B illustrates optics 250 of a confocal imaging apparatus that lacks a field lens, in accordance with one embodiment. The optics 250 may correspond to optics of confocal imaging apparatus 20 of FIG. 1A, such as confocal focusing optics 42. Similar to optics 200, optics 250 include an illumination module 38, a unidirectional mirror (or beam splitter) 40, and a series of lens groups. The series of lens groups include a first lens group 255 with a fixed position and a second lens group 265 that is movable along an imaging axis 280 corresponding to a direction of propagation for an array of light beams 270.

The array of light beams 270 are focused onto a curved focal surface 275. Though the optics 250 are not telecentric, magnification is preserved (fixed) with changes in focusing settings because the array of light beams are collimated between first lens group 255 and second lens group 265. For optics 250, axial gain is 1×. Accordingly, a displacement of 1 mm of the second lens group 265 causes a displacement of the curved focal surface of 1 mm.

An object may be placed along the beam path to be imaged. The array of light beams 285 reflect off of the object and an array of returning light beams return back through the series of lens groups. The array of returning light beams 285 is then reflected by the unidirectional mirror (or beam splitter) 40 onto detector 68. As shown, the optics 250 lack a field lens between the unidirectional mirror or beam splitter 40 and the illumination module 38 and further lack a field lens between the unidirectional mirror or beam splitter 40 and the detector 68. Accordingly, the focal surface for the optics 250 is a curved focal surface 275.

Embodiments have been discussed herein with reference to a confocal imaging apparatus that lacks a field lens and that has a curved focal surface. However, in some embodiments the confocal imaging apparatus includes one or more field lenses and thus has a flat focal surface. For such embodiments, the confocal imaging apparatus operates in a non-telecentric mode, and magnification at a focal plane changes with changes in focusing settings of the confocal imaging apparatus.

Figure 2C:
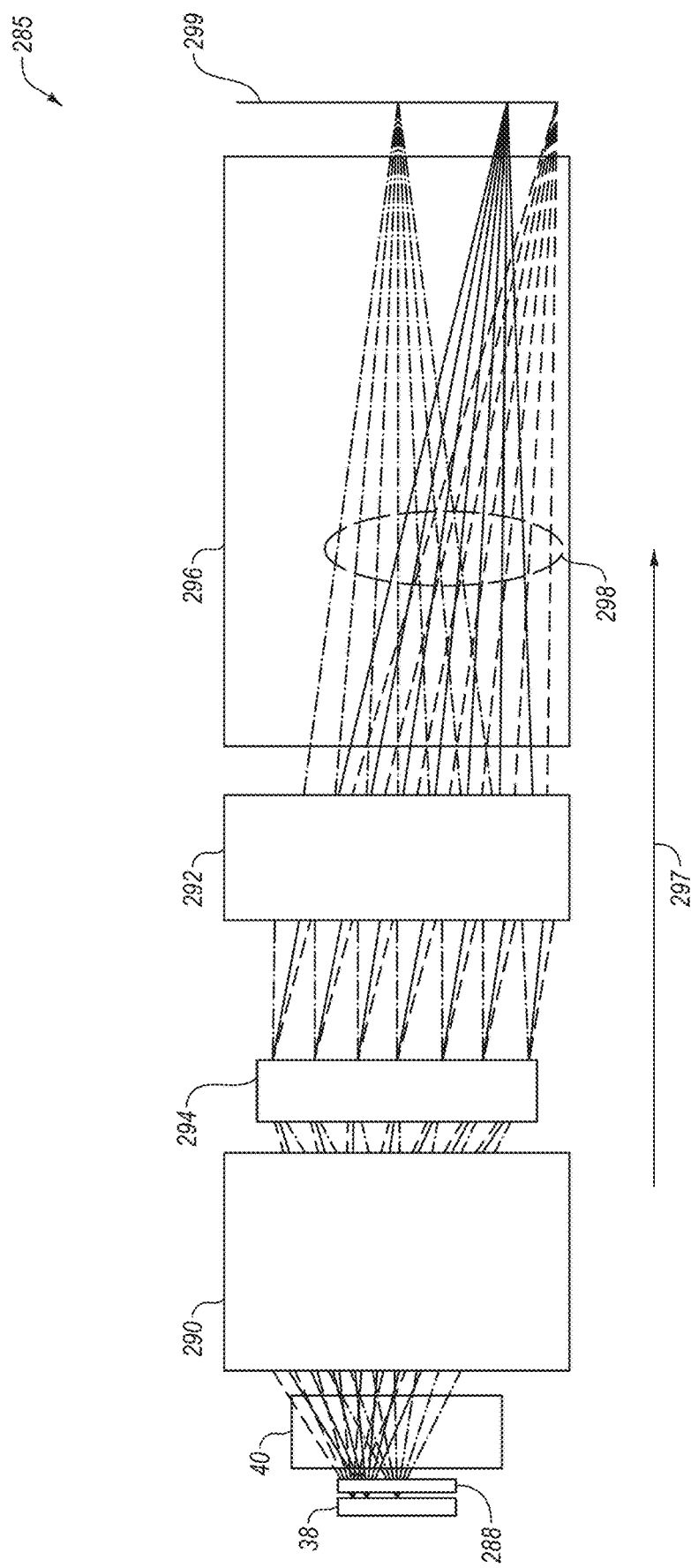
FIG. 2C illustrates optics of a confocal imaging apparatus with a field lens for which changes in a focusing setting cause changes in magnification, in accordance with another embodiment.

FIG. 2C illustrates one example of optics 285 for a confocal imaging apparatus that includes a field lens, in accordance with one embodiment. The optics 285 may correspond to optics of confocal imaging apparatus 20 of FIG. 1A, such as confocal focusing optics 42. Similar to optics 200 and optics 250, optics 285 include an illumination module 38, a unidirectional mirror (or beam splitter) 40, and a series of lens groups. However, optics 285 also include a field lens 288 that causes a flat focal plane 299. The series of lens groups include a first lens group 290 with a fixed position, a second lens group 292 with a fixed position and a third lens group 294 that is movable along an imaging axis 297 corresponding to a direction of propagation for an array of light beams 298.

The array of light beams 298 are focused onto flat focal plane 299. Magnification at the flat foal plane 299 changes with changes in focusing settings. The changes in magnification may introduce significant error into the confocal imaging apparatus. Accordingly, the focusing optics for some large field confocal imaging apparatuses maintain the same magnification with changes in focusing settings (e.g., with changes in a position of one or more lenses along an imaging axis). However, embodiments of the present invention provide a field compensator (see, e.g., field compensator 92 of FIG. 1B) that minimizes or eliminates the error introduced by the change in magnification.

Figure 3A:
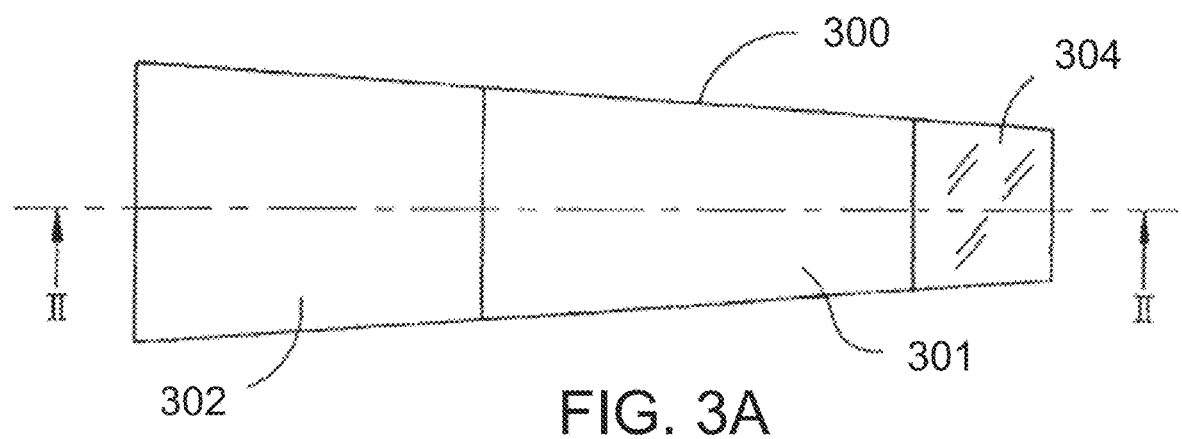
FIG. 3A is a top view of a probing member of a confocal imaging apparatus that includes a prism, in accordance with an embodiment of the invention.
Figure 3B:
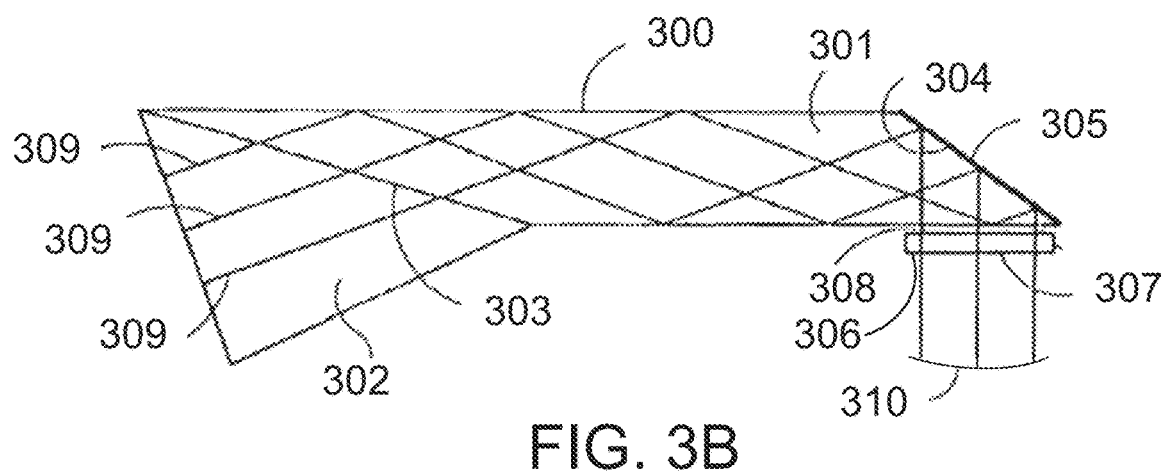
FIG. 3B is a longitudinal cross-section through line II-II of the probing member in FIG. 3A.

FIGS. 3A-3B illustrate a probing member 300 in accordance with one embodiment. The probing member 300 is made of a light transmissive material such as glass. In one embodiment, the probing member 300 acts as a prism and corresponds to prism 220 of FIG. 2. Probing member 300 may include an anterior segment 301 and a posterior segment 302, tightly bonded (e.g., glued) in an optically transmissive manner at 303. Probing member 300 may additionally include a slanted face 304 covered by a reflective mirror layer 305. A window 306 defining a sensing surface 307 may be disposed at a bottom end of the anterior segment 301 in a manner leaving an air gap 308. The window 306 may be fixed in position by a holding structure which is not shown. An array of light rays or beams 309 are represented schematically. As can be seen, the array of light beams 309 are reflected at the walls of the probing member at an angle in which the walls are totally reflective and finally reflect on mirror layer 305 out through the sensing face 307. The array of light beams 309 focus on a non-flat focal surface 310, the position of which can be changed by the focusing optics (not shown in this figure).

Figure 3C:
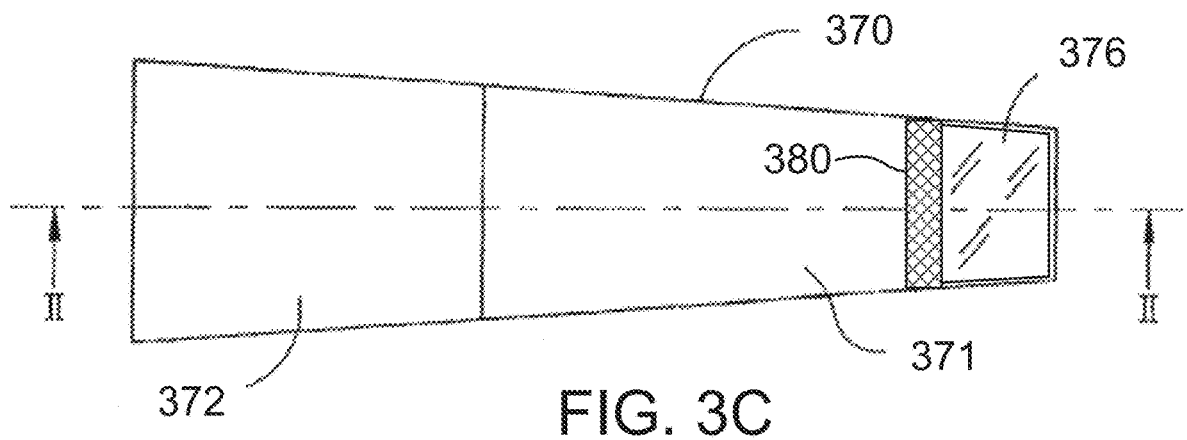
FIG. 3C is a view of a probing member that includes an internal target, in accordance with one embodiment.
Figure 3D:
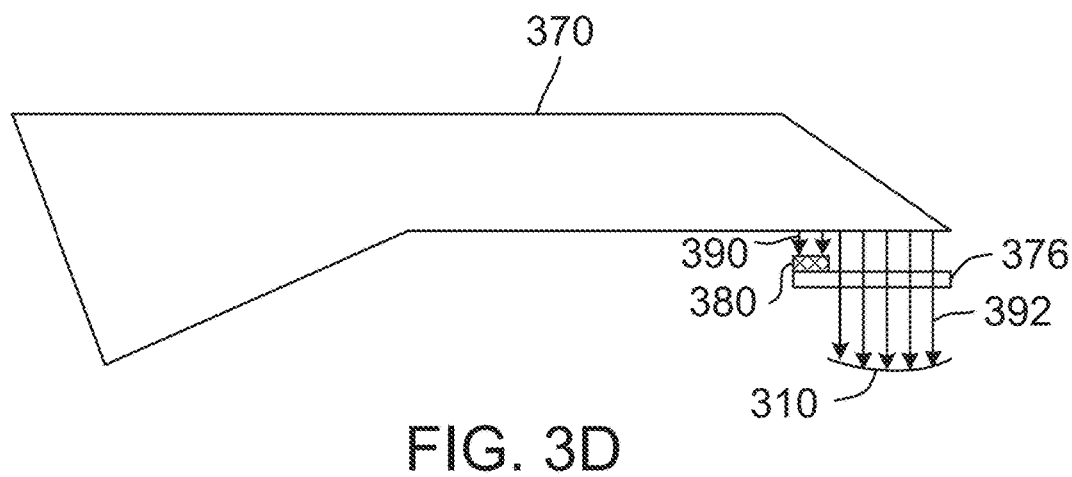
FIG. 3D is a side view of a probing member that includes an internal target, in accordance with one embodiment.

Various components of the confocal imaging apparatus may dissipate considerable amounts of heat relative to a size of the confocal imaging apparatus. For example, the confocal imaging apparatus may include a CMOS sensor and an FPGA, both of which may produce heat. Accordingly, internal temperatures of the confocal imaging apparatus may rise over time during use. At any given time, different portions of the confocal imaging apparatus may have different temperatures. A temperature distribution within the confocal imaging apparatus is referred to as a thermal state of the confocal imaging apparatus. The thermal state of the confocal imaging apparatus may affect various optical parameters. For example, the thermal state may cause the positions of one or more optical components to move within the confocal imaging apparatus due to expansion of the various components in accordance with thermal expansion coefficients of these components. Additionally, the refractive coefficient of one or more lens of the confocal imaging apparatus may change with changes in the thermal state. Such changes cause measurements produced by the confocal imaging apparatus to change with changes in the internal thermal state. Some regions of the confocal imaging apparatus are more sensitive to thermal change than others (e.g., due to a high optical gain). For example, some optical elements may have an axial gain of up to about 7.5 in an embodiment. For such optical elements, a 10 μm movement due to changes in the thermal state could cause up to a 75 μm shift in a measurement. Accordingly, in some embodiments, as shown in FIGS. 3C-3D, an internal target is used to adjust for measurement changes caused by changes in the thermal state. Alternatively, multiple temperature sensors may be disposed within the confocal imaging apparatus and used to determine changes in the thermal state.

FIGS. 3C-3D illustrate a probing member 370 that includes an internal target 380, in accordance with one embodiment. The probing member 370 is substantially similar to probing member 300. For example, probing member 370 may be made of a light transmissive material such as glass, and may act as a prism. Probing member 370 may include an anterior segment 371 and a posterior segment 372, tightly bonded (e.g., glued) in an optically transmissive manner. Probing member 370 may additionally include a slanted face covered by a reflective mirror layer. A window 376 defining a sensing surface may be disposed at a bottom end of the anterior segment 371. The window 376 may be glass or another transparent material, and may be fixed in position by a holding structure which is not shown.

Probing member 370 additionally includes internal target 380 secured to the anterior segment 371 of the probing member 370 within a field of view (FOV) of the probing member 370. The internal target 380 may be a rigid reflective material that will reflect light beams. The internal target 380 may be secured at a fixed position within the probing member 300. Since the internal target 380 is a part of the probing member 370, the location of the internal target 380 should remain constant. In one embodiment, the internal target 380 takes up approximately 500 μm to 1 mm of the FOV.

During measurement, an array of light rays or beams 390-392 is projected out of the anterior segment 371. As can be seen, the internal target 380 is in the path of light beams 390. Accordingly, the light beams 390 are reflected off of the internal target 380, which provides a depth (z-axis) measurement of the internal target 380. Since the internal target 380 is at a fixed position, the measured depth of the internal target 380 should not change. Accordingly, any measured change in the position of the internal target 380 reflects changes in internal optics associated with the thermal state of the confocal imaging apparatus.

The light beams 392 project through the window 376 and focus on a non-flat focal surface 310, the position of which can be changed by the focusing optics (not shown in this figure). Alternatively, the internal target 380 may be included in an imaging apparatus with a flat focal surface (e.g., an imaging apparatus with a field lens). Such an imaging apparatus may or may not be a confocal imaging apparatus. These light beams 392 may be used to measure the position of an object in the FOV of the confocal imaging apparatus. The measured change in the position of the internal target 380 can be used to correct for measurement errors caused by the thermal state. Any apparent change in the z-axis position of the internal target 380 may be used to apply an adjustment factor to other z-axis measurements of the imaged object to compensate for changes in the focusing optics caused by temperature. Additionally, a change in the z-axis position of the internal target may be used to apply an adjustment to the X and Y pixel measurements in embodiments. In one embodiment, the z-axis position of the internal target and measured points of an object are input into a thermal state compensation model to compensate for the thermal state. In one embodiment, the thermal state compensation model is a three dimensional polynomial function.

Figure 4:
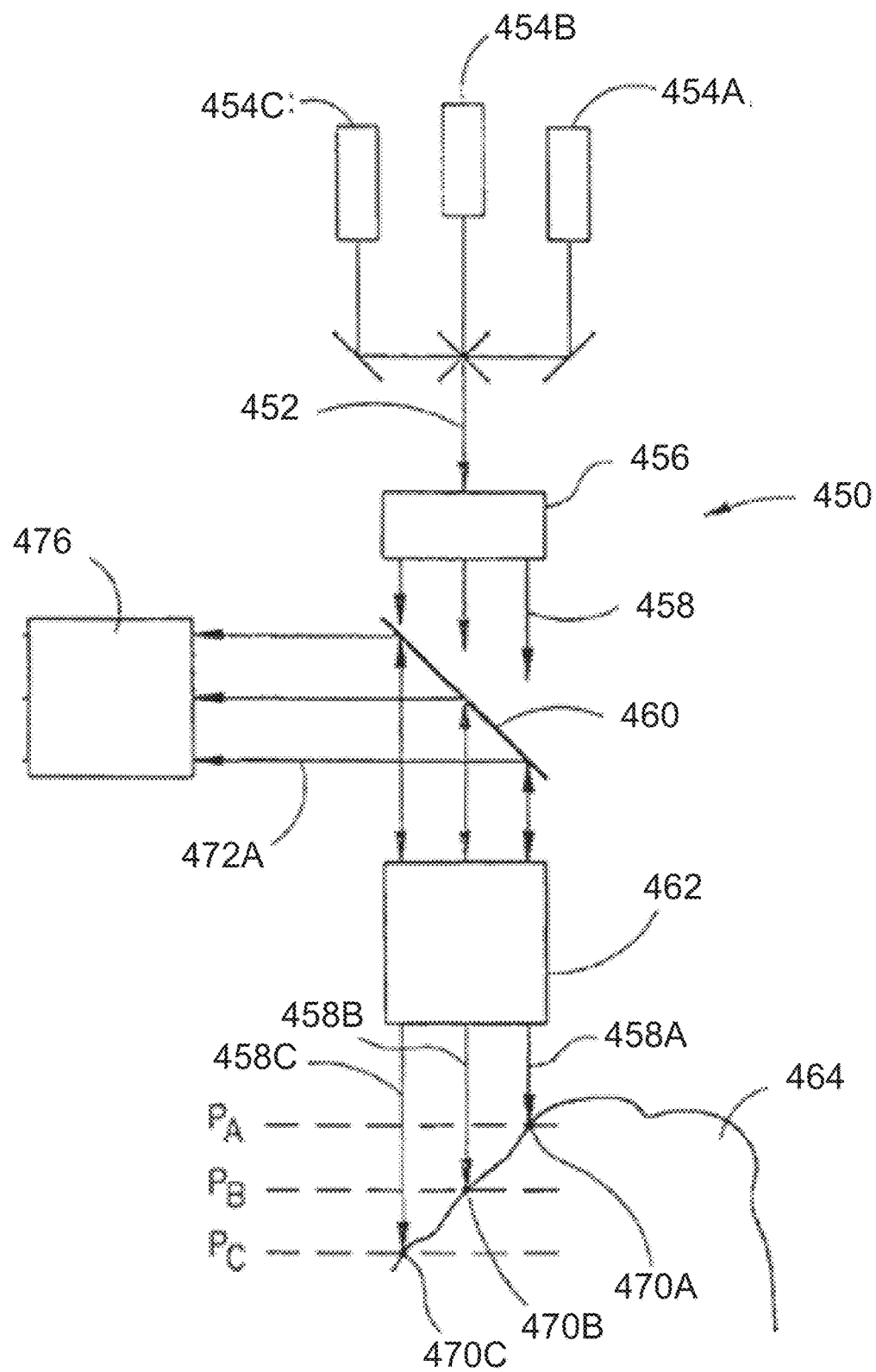
FIG. 4 is a schematic illustration of optics of a confocal imaging apparatus, in accordance with one embodiment.

FIG. 4 is a schematic illustration of a confocal imaging apparatus 450, in accordance with one embodiment. In one embodiment, the confocal imaging apparatus 450 corresponds to confocal imaging apparatus 20 of FIG. 1A. In one embodiment, components of confocal imaging apparatus 20 correspond to like named components illustrated in optics 200 of FIG. 2. In confocal imaging apparatus 450 a parent light beam 452 may be a combination of light emitted by multiple lasers 454A, 454B and 454C. Alternatively, the parent light beam 452 may be produced by a single laser (e.g., 454B). An illumination module 456 (e.g., an optic expander) then expands the single parent beam into an array of incident light beams 458. Incident light beams pass through a unidirectional (e.g., unidirectional) mirror or beam splitter 460, then through focusing optics 462 towards an object 464 to be imaged.

Parent beam 452 may include multiple different wavelengths, with a different wavelength being transmitted from each laser 454A-C. Thus, parent light beam 452 and one or more incident light beams in the array of light beams 458 may be composed of multiple different light components. Alternatively, each light beam in the array of light beams may include a single wavelength from the multiple wavelengths of parent beam 452. Lasers 454A-C may be arranged such that each light beam focuses on a different curved focal surface, $P_A$, $P_B$ and $P_C$, respectively. In the position shown in FIG. 4, incident light beam 458A reflects off of the surface at spot 470A, which in the specific optical arrangement of optics 462 is in the focal point for light component A (emitted by laser 454A). Thus, a returned light beam 472A is measured by a detector 476 that includes a two dimensional array of sensors, each corresponding to a pixel. In one embodiment, the detector is a two-dimensional array of spectrophotometers, e.g. a 3 CHIP COD sensor. Similarly, different maximal intensity will be reached for spots 470B and 470C for light components B and C, respectively. Thus, by using different light components each one focused simultaneously at a different plane, the time used to complete a measurement can be reduced as different focal plane ranges can simultaneously be measured.

In an alternative embodiment, only a single wavelength of light is emitted (e.g., by a single laser). Thus, parent beam 452 and the array of light beams 458 may include a single wavelength. In such an embodiment, each of the light beams in the array of light beams 458 focuses on the same curved focal surface $P_C$. Thus in the position shown in FIG. 4, incident light beam 458A reflects off of the surface at spot 470A which in the specific focusing setting of focusing optics 462 is at the focal point for focusing optics 462. Thus, the returned light beam 472A is measured by a detector 476 that includes a two dimensional array of sensors, each corresponding to a pixel and is registered as the z-axis position for spot 470C. Similarly, incident light beams 458A, 458B reflect off of the surface at spots 470A and 470B, respectively. However, the spots 470A, 470B are not on the curved focal surface $P_C$. Accordingly, light is reflected back in a blurred manner from the object 464 for those spots. By changing the focusing setting for focusing optics 462 so that the focal point aligns with spot 470B and separately with 470A, corresponding depths associated with those focusing settings may be detected for spots 470B and 470A, respectively.

Figure 5A:
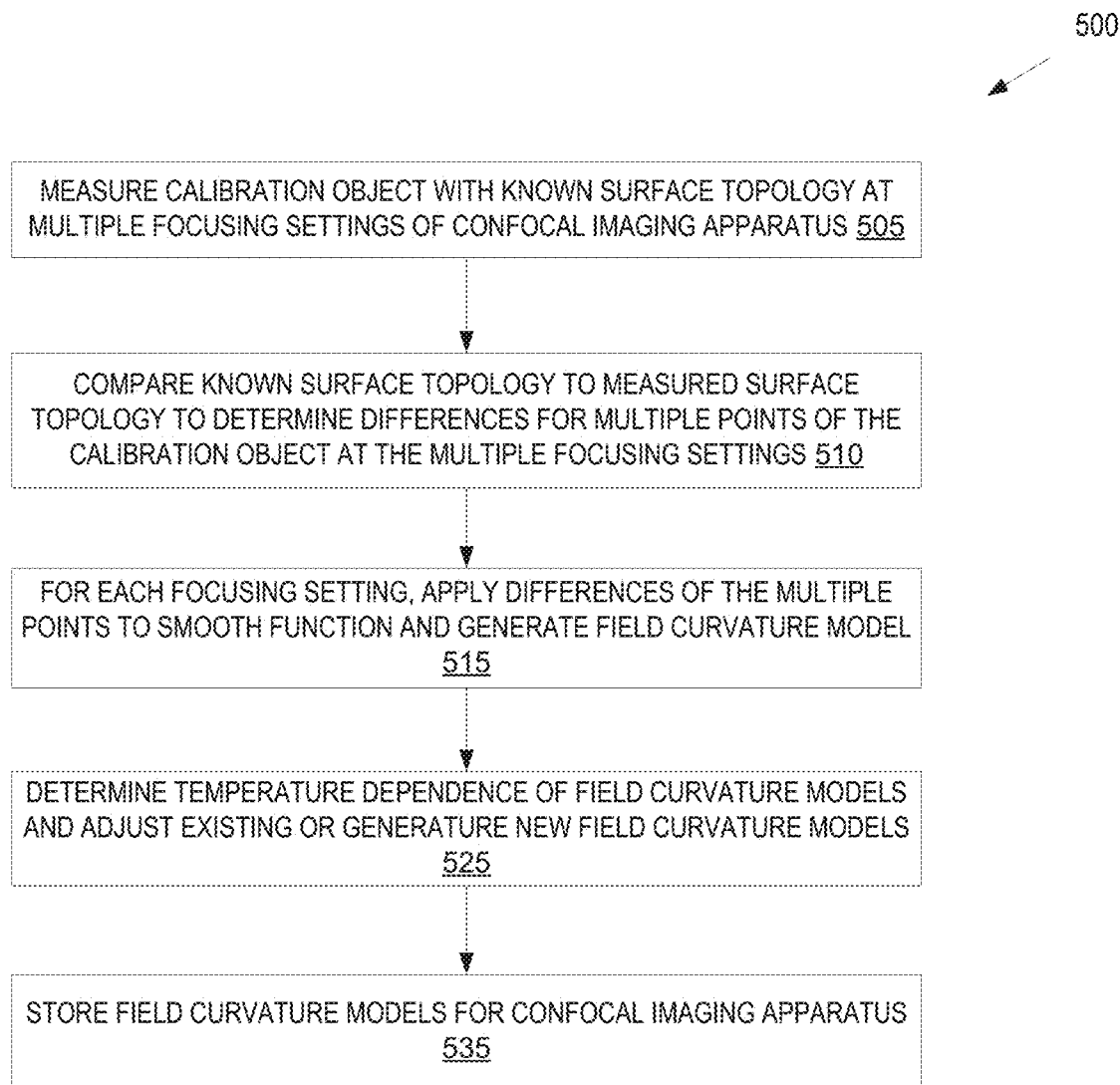
FIG. 5A is a flow chart showing one embodiment of a method for calibrating a confocal imaging apparatus having an imaginary non-flat focal surface.

FIG. 5A is a flow chart showing one embodiment of a method 500 for calibrating a confocal imaging apparatus having an imaginary non-flat focal surface. Method 500 may be performed by processing logic that may comprise hardware (e.g., circuitry, dedicated logic, programmable logic, microcode, etc.), software (e.g., instructions run on a processing device to perform hardware simulation), or a combination thereof. In one embodiment, at least some operations of method 500 are performed by a computing device (e.g., computing device 24 of FIG. 1B). In one embodiment, at least some operations of method 500 are performed by confocal imaging apparatus 20 of FIG. 1A.

The confocal imaging apparatus described in embodiments herein has a non-flat (e.g., curved) focal surface. This curved focal surface introduces inaccuracies in depth measurements of points of a scanned object. For example, a first point of the object at a center of the confocal imaging apparatus' imaging field may be in focus and thus cause a highest intensity measurement at a depth $Z_i$. However, a second point of the object at an edge of the imaging field that has a same depth as the first point may be in focus and cause a highest intensity measurement at a depth $Z_i+X$ due to the non-flat focal surface, where X represents the difference between the focal point at the center of the imaging field and the focal point at the edge of the imaging field. Thus, the non-flat imaging field will cause measurements of the first and second points to yield different depth values even though they are at the same depth. In one embodiment, calibration method 500 is performed to calibrate the confocal imaging apparatus so that the error introduced by the non-flat focal surface can be eliminated.

At block 505 of method 500, a calibration object is measured by the confocal imaging apparatus. The calibration object is a high accuracy object with known X, Y and Z coordinates for every point of the calibration object. The accuracy level of the calibration object may define the final accuracy of the confocal imaging apparatus. In one embodiment, the X, Y and Z coordinates for the calibration object are accurate and known to a level of accuracy that is a degree of magnitude higher than a final desired accuracy of the confocal imaging apparatus. For example, if the confocal imaging apparatus is to have a final accuracy to 5 microns, then the calibration object may be accurate to 0.5 microns.

Various calibration objects may be used, a few examples of which are set forth herein. One example calibration object is a sphere with a very accurate radius on an accurate X–Y–Z stage. Another example calibration object is a flat plate with a grid of horizontal and vertical lines printed on a surface of the plate. A flatness of the plate and the line spacing may be very accurate. Another example calibration object is a flat plate with circles or dots printed on a surface of the plate. The flatness of the plate and the size and spacing of the circles may be very accurate. Many other calibration objects may also be used. FIG. 5C illustrates one example calibration object 590, which is a flat plate with a grid of precisely spaced circles or dots.

Referring back to FIG. 5A, the calibration object is measured at each focusing setting (e.g., encoder position) of the confocal imaging apparatus. For some types of calibration objects (e.g., the sphere), the calibration object is moved to multiple different X, Y positions for each focusing setting and/or to multiple different X, Y, Z positions for each focusing setting. For other types of calibration objects (e.g., the plates), the calibration object may be moved to multiple different Z positions for each focusing setting. Measurements may be taken for each position of the calibration object.

In one embodiment, the calibration object is mounted to a calibration jig, which may precisely move the calibration object in one or more dimensions. For example, the calibration object 590 may be mounted to the calibration jig, and the calibration jig may be moved along the z-axis. In one embodiment, the calibration jig moves the calibration object in 1 mm increments, with an accuracy of 1 µm. The calibration jig may move the calibration object in such a way as to cover more than the full field of view of the confocal imaging apparatus (e.g., the calibration object may be larger than the FOV of the confocal imaging apparatus) and to cover more than the range for the depth of scanning of the confocal imaging apparatus.

In the example of the calibration object 590, the calibration object 590 may be scanned in two ways. A first scan may be performed at each depth position of the calibration object 590 using regular confocal scanning. This will provide a z-position for each dot in the coordinate system of the confocal imaging apparatus (e.g., based on the coordinates of the encoder that positions the lens). A second scan may be performed to generate an image of the dots at focus for each focal setting. The image may be used to determine an X, Y position for the center of each dot in pixel coordinates and with sub-pixel accuracy.

At block 510, the measurements of the calibration object (measurements of the calibration object's surface topology) are compared to a known surface topology of the calibration object. Each point in the calibration object (e.g., each dot in calibration object 590 having a measured x-pixel, y-pixel and encoder value) may be paired to a corresponding real world point (point in a world coordinate system) from the calibration object, where the world coordinate system corresponds to known X, Y, Z coordinates of the calibration object. For example, the X and Y coordinates for calibration object 590 would correspond to known fixed positions of the dots, and the Z coordinate for calibration object 590 would depend on a setting of a calibration jig. For each point of the calibration object, a difference between a measured depth value and a known depth value may be determined. Additionally, for each point of the calibration object, a difference between a measured X and Y position and a known X and Y position may be determined. This may be performed for each focusing setting of the confocal imaging apparatus.

At block 515, the determined differences of the multiple points may be applied to a smooth function (e.g., to a polynomial function such as a three dimensional polynomial function) that may be used to model the field curvature of the confocal imaging apparatus' non-flat focal surface. The function is referred to herein as a un-distortion function. In one embodiment, the determined differences are applied to solve for the constants in a bivariate quadratic polynomial of the form:

$$Z_{Field\ Curvature\ (object)}(x,y,Z_{optics}) = a_1 x^2 + a_2 y^2 + a_3 x + a_4 y + a_5 xy + a_6 \qquad (1)$$

Where x and y are the X, Y coordinates for points on a plane normal to the imaging axis. Alternatively, a higher order polynomial may be used. The smooth function with the solved constants may then be used as an accurate field curvature model. Every parameter may be a polynomial that depends on the focusing setting (z-axis value) of the confocal imaging apparatus. This may result in an 18 parameter field curvature model if the above described bivariate quadratic polynomial is used.

Alternatively, the determined differences may be applied to solve for the constants in another smooth function (e.g., a function describing a conic shape). In such an embodiment, a generated model may have a different number of parameters (e.g., 12 parameters if a function describing a conic shape is used). Linear minimization methods (e.g., linear least square method) and/or non-linear minimization methods (e.g., Broyden-Fletcher-Goldfarb-Shanno (BFGS) method) may be applied to find the best values for the constants. As mentioned, this process may be performed for each focusing setting. This is because the amount of field curvature may change with different focusing settings of the confocal imaging apparatus. Accordingly, a separate field curvature model may be generated for each focusing setting. Alternatively, a single field curvature model may be generated that accounts for the changes to the field curvature model due to changes in the focusing setting.

In embodiments, X and Y positions are solved for at the same time that the depth is solved for. For example, differences in X and Y position at different focus settings may also be applied to solve for the constants in the smooth function. Additionally, other types of geometric correction may be solved for as well using this technique. All such geometric corrections may be solved for together. Other types of phenomena that may be corrected for using this technique include magnification change, optical distortion (e.g., non-constant magnification in x and y), optical aberrations, and so on. All such distortions may be solved for together.

Figure 5B:
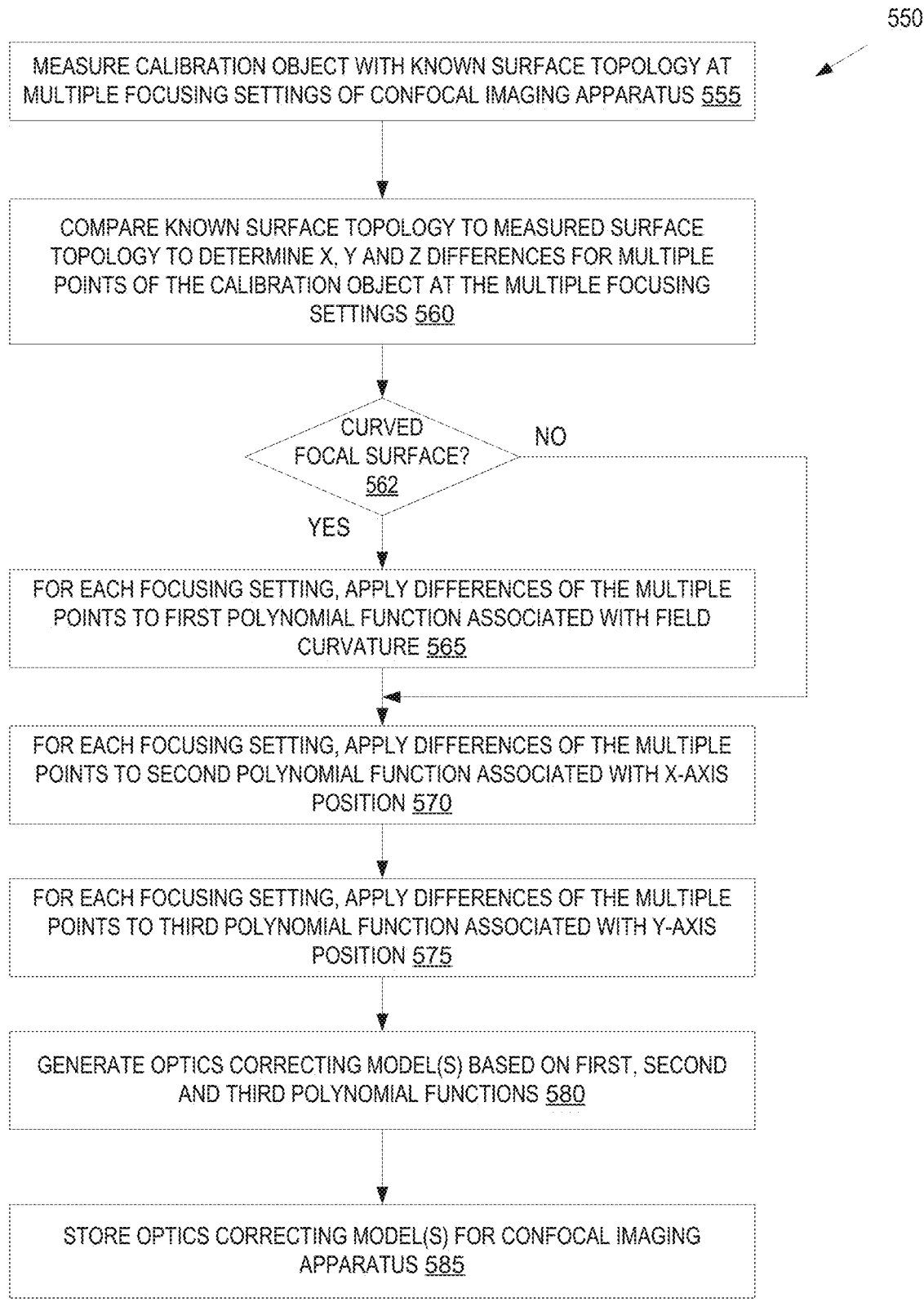
FIG. 5B is a flow chart showing one embodiment of a method for calibrating a confocal imaging apparatus for which changes in a focusing setting cause changes in magnification.
Figure 5C:
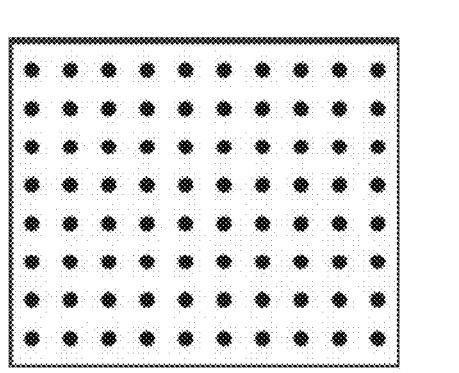
FIG. 5C illustrates one example calibration object, in accordance with one embodiment.
Figure 5D:
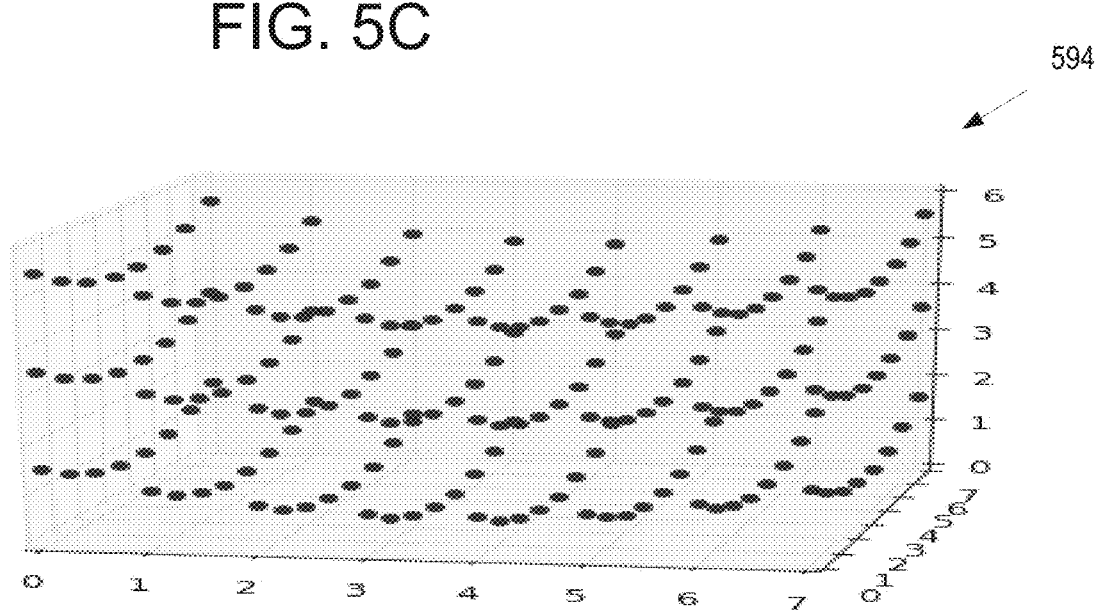
FIG. 5D illustrates a chart showing a distribution of points of a calibration object as measured by a confocal imaging apparatus, in accordance with one embodiment.
Figure 5E:
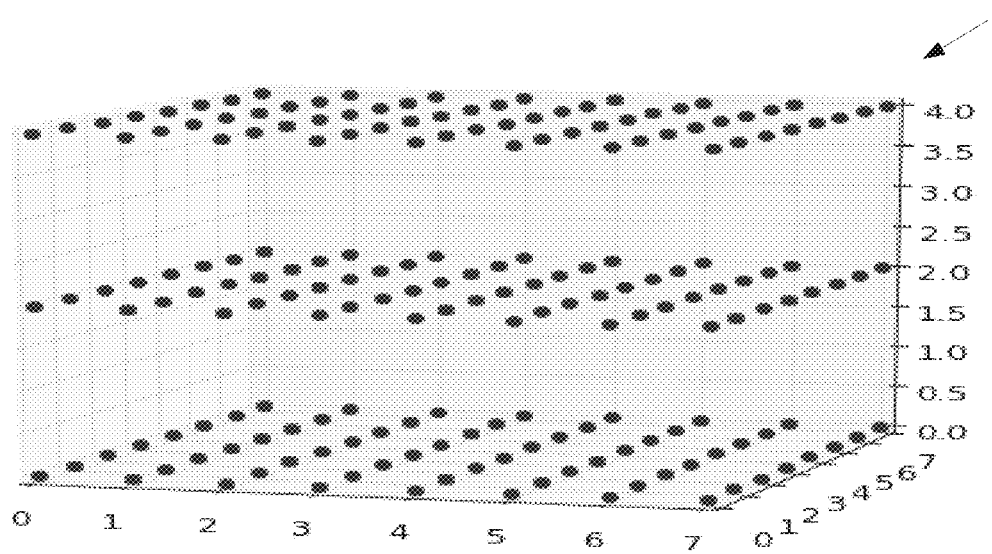
FIG. 5E illustrates a chart showing a distribution of points in a world coordinate system, in accordance with one embodiment.

FIG. 5D illustrates a chart 594 showing a distribution of points of the calibration object 590 as measured by the confocal imaging apparatus (in the coordinate system of the confocal imaging apparatus). Chart 594 shows measurements taken with the calibration object 590 at three different z positions. As shown, the dots appear to lie on a curved surface. FIG. 5E illustrates a chart 597 showing a distribution of points in the real world. Chart 597 shows measurements taken with the calibration object 590 at three different z positions. As shown, the dots lie on a plane. After calibration, the transformation for each dot may be determined to correct for optical distortions. Thus, the true world position of each dot may be accurately measured.

At block 525, a temperature dependence of the confocal imaging apparatus (e.g., the focusing optics and of a lens housing for the focusing optics) is determined. In one embodiment, the operations of one or more of blocks 505-515 are performed at multiple temperatures over a temperature operating range of the confocal imaging apparatus to determine the temperature dependence. Changes in temperature may cause differences in the measured depth values. Accordingly, a temperature dependency may be determined and applied to the field curvature model to create a thermal state correction model. For example, the field curvature model may be modified from x, y, z=F(i, j, encoder) to x, y, z=F(i, j, encoder, $T_{state}$), where x, y and z represent real world coordinates, i represents an x-pixel, j represents a y-pixel, encoder represents a focal setting (encoder position), and $T_{state}$ represents a thermal state. For such a model that takes into account the thermal state, an estimate of the thermal state should be obtained for each measurement. A thermal state correction model may also be generated for an imaging apparatus with a flat focal surface using the same process as described herein for an imaging apparatus with a curved focal surface.

In one embodiment, opto-mechanical simulation is performed to determine a relationship between temperature and adjustments in calibration of the focusing optics. This relationship may be used to determine a correction that may be applied to all parameters of the generated field curvature model or models, where the amount of correction is based on a current temperature.

In one embodiment, the main change in the focusing optics due to temperature is a focus shift. Curvature of the non-flat focal surface may be practically unchanged by changes in temperature. In one embodiment, a shift in focus for focusing settings may be determined by scanning one or more elements (e.g., an internal target such as internal target 380 of FIGS. 3C-3D) of the confocal imaging apparatus that is near or along the optical path. In one embodiment, the scanned element is on a side of a field of view (FOV) of the confocal imaging apparatus. This element may be kept at the same distance relative to one or more components of the focusing optics. With each scan, when the 3D surface of an object is captured, the edge of the FOV where the internal target is located captures a position of the internal target. Due to the fact that the internal target is part of the confocal imaging apparatus and has a fixed position, detected changes in the position of the internal target are caused by changes in the thermal state. Accordingly, if a focus shift of the internal target is detected from the scan, then an adjustment factor may be applied to the field curvature model to compensate for the thermal state.

In one embodiment, separate field curvature models are generated for each temperature value or range of the confocal imaging apparatus at a particular focusing setting. Alternatively, a single model may be generated for each focusing setting that accounts for changes in temperature. Alternatively, a temperature dependent adjustment factor may be determined and applied to the field curvature model or models based on a measured temperature.

In one embodiment, a simple model may be used that assumes that optical change caused by the thermal state is primarily due to a linear shift in the focal setting (e.g., a backward motion in the encoder position). For such a model, changes caused by the thermal state may be corrected by adding the difference between a current measured internal target position and a reference value to every focal setting (encoder value) before applying the un-distortion function. The simple model may have the form of:

$$x,y,z=F(i,j,\text{encoder}-(\text{internal target position}-\text{reference target position})) \quad (2)$$

where F is the un-distortion function, such as function (1) above.

In another embodiment, a more complex model is used that assumes internal target effects are caused by the focal shift of encoder, but in a complex way. Such a model may have the form of:

$$x,y,z=F(i,j,f(\text{encoder},\text{internal target position})) \quad (3)$$

In another embodiment, a model that corrects for distortions caused by the thermal state assumes that the thermal state changes all optics by a small amount that can be linearly estimated. Such a model may have the form of:

$$x, y, z = F_{hot}(i, j, \text{encoder})\frac{(p-a)}{(b-a)} + F_{cold}(i, j, \text{encoder})\left(1 - \frac{(p-a)}{(b-a)}\right) \quad (4)$$

where $F_{hot}$ is the un-distortion function under a hot condition, $F_{cold}$ is the un-distortion function under a cold condition, a is the internal target position in the hot condition, b is the internal target position in the cold position, and p is the measured internal target position.

At block 535, the one or more generated field curvature models for the confocal imaging apparatus are stored. The field curvature models may be stored in a memory of the confocal imaging apparatus and/or in a memory of a computing device that processes data from the confocal imaging apparatus. In one embodiment, the field curvature models are stored in a nonvolatile memory (e.g., a read only memory (ROM), FLASH, or other nonvolatile memory) of the confocal imaging apparatus. The Field curvature model (or models) may be applied to measurements of the confocal imaging apparatus to correct the error in the depth measurements that are introduced by the non-flat focal surface of the confocal imaging apparatus. If calibration information is stored in memory of the confocal imaging apparatus, then the field curvature models may be sent along with measurement data to a computing device when measurements are taken. The computing device may then use the received field curvature models to correct for the field curvature of the confocal imaging apparatus.

FIG. 5B is a flow chart showing one embodiment of a method 550 for calibrating a confocal imaging apparatus for which changes in a focusing setting cause changes in magnification. Method 550 may be performed by processing logic that may comprise hardware (e.g., circuitry, dedicated logic, programmable logic, microcode, etc.), software (e.g., instructions run on a processing device to perform hardware simulation), or a combination thereof. In one embodiment, at least some operations of method 550 are performed by a computing device (e.g., computing device 24 of FIG. 1B). In one embodiment, at least some operations of method 550 are performed by confocal imaging apparatus 20 of FIG. 1A.

The confocal imaging apparatus described with reference to method 550 may have a non-flat (e.g., curved) focal surface or a flat focal plane. Moreover, the confocal imaging apparatus described with reference to method 550 has focusing optics that are configured so that changes in a focusing setting cause a change in magnification at the focal surface or focal plane. This change in magnification introduces inaccuracies in X and Y position measurements of points of a scanned object. For example, a point of the object might be measured to have a first X and Y position at a first focusing setting, but might be measured to have a second X and Y position at a second focusing setting. Thus, the magnification changes will cause measurements to yield different X, Y values as the focusing setting changes. In one embodiment, calibration method 550 is performed to calibrate the confocal imaging apparatus so that the inaccuracies introduced by the changes in magnification can be eliminated.

At block 555 of method 500, a calibration object is measured by the confocal imaging apparatus. The calibration object is a high accuracy object with known X, Y and Z coordinates for every point of the calibration object. The accuracy level of the calibration object may define the final accuracy of the confocal imaging apparatus. In one embodiment, the X, Y and Z coordinates for the calibration object are accurate and known to a level of accuracy that is a degree of magnitude higher than a final desired accuracy of the confocal imaging apparatus. For example, if the confocal imaging apparatus is to have a final accuracy to 5 microns, then the calibration object may be accurate to 0.5 microns. Any of the calibration objects described with reference to FIG. 5A may be used.

The calibration object is measured at each focusing setting (encoder value) of the confocal imaging apparatus. For some types of calibration objects (e.g., the sphere), the calibration object is moved to multiple different X, Y positions for each focusing setting and/or to multiple different X, Y, Z positions for each focusing setting. For other types of calibration objects (e.g., the plates), the calibration object may be moved to multiple different Z positions for each focusing setting. Measurements may be taken for each position of the calibration object. Based on these measurements, a list of coordinates is collected in both the calibration object space (e.g., real world) and in the sensor/optics space (e.g., virtual space). In the calibration object space, each set of coordinates for a point of the object has an $X_{obj}$, $Y_{obj}$ and $Z_{obj}$ coordinate. These coordinates are known to be accurate due to the known information about the calibration object. In the sensor/optics space, each set of coordinates for a point of the object includes an $X_{pix}$, $Y_{pix}$, $Z_{optics}$ coordinate, where $X_{pix}$ and $Y_{pix}$ are determined based on the pixel detecting the point and $Z_{optics}$ is the lens position of the focusing optics (e.g., the focusing setting).

At block 560, the measurements of the calibration object (measurements of the calibration object's surface topology) may be compared to a known surface topology of the calibration object. For each point of the calibration object, a difference between a measured depth value, X value and/or Y value and a known depth value, X value and/or Y value may be determined. This may be performed for each focusing setting of the confocal imaging apparatus.

At block 562, it is determined whether the focusing optics have a curved focal surface. If the focusing optics do have a curved focal surface, the method proceeds to block 565. Otherwise the method proceeds to block 570.

At block 565, the determined differences of the multiple points for the X, Y and/or Z coordinates may be applied to a smooth function (e.g., to a polynomial function such as a three dimensional polynomial function) that may be used to model the field curvature of the confocal imaging apparatus' non-flat focal surface. In one embodiment, the determined differences are applied to solve for the constants in a bivariate quadratic polynomial of the form:

$$Z_{Field\ Curvature\ (object)}(x,y,Z_{optics})=a_1x^2+a_2y^2+a_3x+a_4y+a_5xy+a_6 \qquad (5)$$

Where x and y are the $X_{pix}$, $Y_{pix}$ coordinates in the sensor space. Alternatively, the determined differences may be applied to solve for the constants in another smooth function (e.g., a function describing a conic shape), such as a polynomial of higher order. The smooth function with the solved constants may then be used for an accurate field curvature model.

At block 570, the determined differences of the multiple points for the X, Y and/or Z coordinates may be applied to a smooth function (e.g., to a polynomial function such as a three dimensional or higher dimensional polynomial function) that may be used to model the changes in magnification of the confocal imaging apparatus on an x-axis caused by changes in the focusing setting (e.g., changes in the $Z_{optics}$ value). In one embodiment, the determined differences are applied to solve for the constants in a bivariate quadratic polynomial of the form:

$$X_{Object}(x,Z_{optics})=b_1x^2+b_2y^2+b_3x+b_4y+b_5xy+b_6 \qquad (6)$$

Where x and y are the $X_{pix}$, $Y_{pix}$ coordinates in the sensor space. Alternatively, the determined differences may be applied to solve for the constants in another smooth function (e.g., in another three dimensional polynomial function, such as a function describing a conic shape). The smooth function with the solved constants may then be used as an accurate magnification compensation model for the X coordinate.

At block 575, the determined differences of the multiple points for the X, Y and/or Z coordinates may be applied to a smooth function (e.g., to a polynomial function such as a three dimensional polynomial function) that may be used to model the changes in magnification of the confocal imaging apparatus on a y-axis caused by changes in the focusing setting (e.g., changes in the $Z_{optics}$ value). In one embodiment, the determined differences are applied to solve for the constants in a bivariate quadratic polynomial of the form:

$$Y_{Object}(x,y,Z_{optics})=c_1x^2+c_2y^2+c_3x+c_4y+c_5xy+c_6 \qquad (7)$$

Where x and y are the $X_{pix}$, $Y_{pix}$ coordinates in the sensor space. Alternatively, the determined differences may be applied to solve for the constants in another smooth function (e.g., in another three dimensional polynomial function, such as a function describing a conic shape). The smooth function with the solved constants may then be used as an accurate magnification compensation model for the Y coordinate.

Blocks 565, 570 and 575 have been described as three separate operations. However, in some embodiments a single operation may be performed to solve for each of the x-coordinate, the y-coordinate and the z-coordinate. For example, an un-distortion function having the following form may be solved to determine the x, y and z coordinates.

$$F_X(x,y,z) = a_0 + a_1 x + a_2 y + a_3 z + a_4 x^2 + a_5 y^2 + a_6 z^2 + \ldots + a_i xy + \ldots + a_j x^n y^m z^k$$

$$F_Y(x,y,z) = b_0 + b_1 x + b_2 y + b_3 z + b_4 x^2 + b_5 y^2 + b_6 z^2 + \ldots + b_i xy + \ldots + b_j x^n y^m z^k$$

$$F_Z(x,y,z) = c_0 + c_1 x + c_2 y + c_3 z + c_4 x^2 + c_5 y^2 + c_6 z^2 + \ldots + c_i xy + \ldots + c_j x^n y^m z^k \quad (8)$$

where $F_X$, $F_Y$ and $F_Z$ are the functions whose results in world coordinates are to be solved for, x and y are pixel coordinates measured by the confocal imaging apparatus, z is a focal setting (e.g., encoder coordinates corresponding to a focal setting), $a_i$, $b_i$ and $c_i$ are learned parameters, and n, m and k are the maximal degree of the nominal. The function may be selected to minimize a mean square error between the world coordinates and the found positions after the function transformation. Outlier positions may be detected and removed before fitting. In one embodiment, a number of non-zero parameters is constrained.

At block 580, one or more optics correcting models are generated based on the first second and third polynomial functions (or other smooth functions), such as those represented in equations 5-8. Every parameter for equations 5-8 may be a polynomial that depends on the focusing setting (z-axis value) of the confocal imaging apparatus. In one embodiment, each parameter is modeled as a quadratic change to the $Z_{optics}$ (focusing setting). For example, parameter $a_1$ may be a parameter having a form:

$$a_1(Z_{Optics}) = A + B^* Z_{Optics} + C^* Z_{Optics}^2 \quad (9)$$

Parameters $a_2$–$a_6$, $b_1$–$b_6$ and $c_1$–$c_6$ may be similarly represented. This may result in a 54 parameter model that corrects for full curvature, magnification and distortion of the field of view (FOV).

Linear minimization methods (e.g., linear least square method) and/or non-linear minimization methods (e.g., Broyden-Fletcher-Goldfarb-Shanno (BFGS) method) may be applied to find the best values for the constants at each of blocks 565, 570 and 575. As mentioned, these processes may be performed for each focusing setting. This is because the amount of field curvature and magnification may change with different focusing settings of the confocal imaging apparatus. Accordingly, a separate model may be generated for each focusing setting. Alternatively, a single model may be generated that accounts for the changes to the model due to changes in the focusing setting. Note that temperature dependence may also be determined and included in the model as described with reference to block 525 of method 500. In one embodiment, a temperature dependence is determined, and a model that corrects for thermal state is created, as discussed above with reference to method 500.

At block 585, the one or more generated models for the confocal imaging apparatus are stored. The models may be stored in a memory of the confocal imaging apparatus and/or in a memory of a computing device that processes data from the confocal imaging apparatus. In one embodiment, the models are stored in a nonvolatile memory (e.g., a read only memory (ROM), FLASH, or other nonvolatile memory) of the confocal imaging apparatus. The model (or models) may be applied to measurements of the confocal imaging apparatus to correct the error in the depth measurements that are introduced by the non-flat focal surface as well as to correct for inaccuracies caused by changes in magnification. If calibration information is stored in memory of the confocal imaging apparatus, then the models may be sent along with measurement data to a computing device when measurements are taken. The computing device may then use the received models to correct for the field curvature and/or magnification changes of the confocal imaging apparatus.

Figure 6:
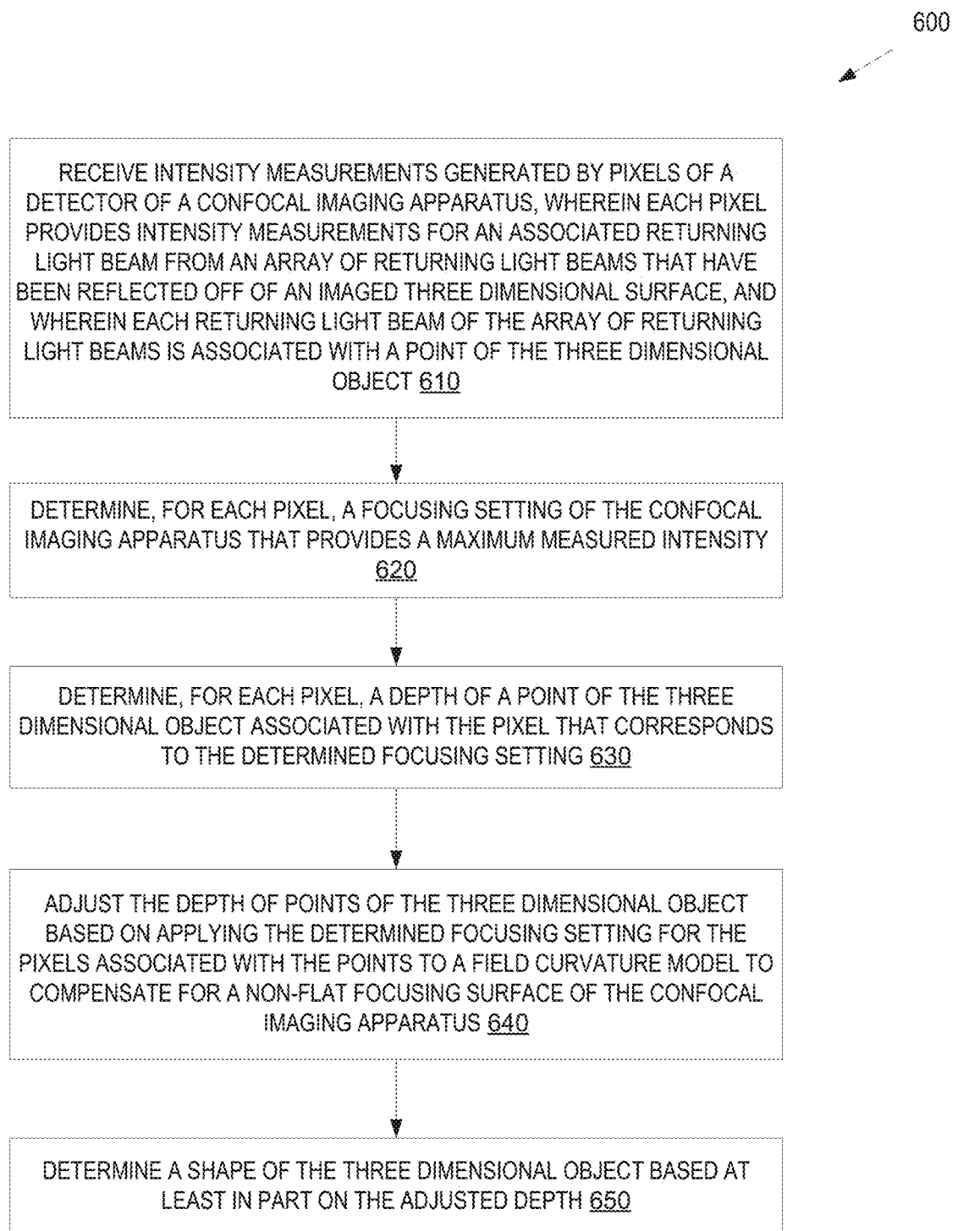
FIG. 6 is a flow chart showing one embodiment of a method for adjusting depth measurements of a scanned three dimensional object based on application of a field curvature model calibrated to a confocal imaging apparatus.

FIG. 6 is a flow chart showing one embodiment of a method 600 for adjusting depth measurements of a scanned three dimensional object based on application of a field curvature model or other model (e.g., a thermal state compensation model) calibrated to a confocal imaging apparatus or other imaging apparatus (e.g., a stereoscopic imaging apparatus). Method 600 may be performed by processing logic that may comprise hardware (e.g., circuitry, dedicated logic, programmable logic, microcode, etc.), software (e.g., instructions run on a processing device to perform hardware simulation), or a combination thereof. In one embodiment, at least some operations of method 600 are performed by a computing device (e.g., computing device 24 of FIG. 1B executing image processing module 82).

At block 605 of method 600, processing logic receives intensity measurements generated by pixels of a detector of a confocal imaging apparatus. The detector may have a two-dimensional array of pixels, and each pixel may receive a particular light beam of an array of light beams directed at the detector. The array of light beams may be an array of returning light beams that have been reflected off of a surface of the imaged three dimensional object. Thus, each pixel of the detector is associated with a particular point of the three dimensional object and provides intensity measurements for an associated returning light beam from the array of returning light beams.

Each received intensity measurement is associated with a particular focusing setting of the confocal imaging apparatus. Intensity measurements may be received over a range of focusing settings. At block 620, processing logic determines, for each pixel, a focusing setting of the confocal imaging apparatus that provides a maximum measured intensity.

A relative distance between a probe of the confocal imaging apparatus and a focal point of the confocal imaging apparatus may be known for each focusing setting (encoder value). A point of the imaged object is known to be in focus (e.g., at the focal point) when a measured intensity for that point is maximal. Accordingly, at block 630 processing logic determines, for each pixel, a depth of a point of the three dimensional object associated with that pixel that corresponds to the focusing setting that yielded the maximal intensity. If the imaging apparatus includes an internal target in the FOV of the imaging apparatus, then some pixels will be associated with points on the internal target. Accordingly, a depth of the points of the internal target may also be determined.

As discussed previously herein, the non-flat focal surface and/or magnification changes of the confocal imaging apparatus introduce an error in the depth measurements and/or in the X, Y coordinate measurements. Accordingly, at block 640 processing logic adjusts the determined depths of points of the imaged three dimensional object based on applying the determined focusing settings for the pixels associated with those points to a field curvature model. Processing logic may additionally or alternatively determine X, Y coordinates of the points based on applying the determined focusing settings to the field curvature model or other model. One or more field curvature models and/or other models may be used. For example, a particular field curvature model and/or other model may be associated with each focusing setting. An appropriate field curvature model may be identified based on the focusing setting at which a point on the object came into focus. A particular depth adjustment for that point may then be determined by providing the X, Y coordinates of the pixel into the determined field curvature model. Alternatively, a single field curvature model may be used, and the X, Y coordinates and focusing setting may be input into the field curvature model to determine the depth displacement. In one embodiment, a temperature of the focusing optics is also measured and/or a thermal state is otherwise determined (e.g., using an internal target position), and an additional depth adjustment factor (and/or other optical adjustment) is determined based on the temperature (e.g., using a thermal state compensation model). This additional depth adjustment factor (and/or additional optical adjustment) may then be applied to the measured depths (and/or X and Y coordinates) of all points. In one embodiment, a single model is used that compensates for both the thermal state and field curvature.

At block 650, processing logic may determine a shape (e.g., surface topology) of the three dimensional object based on the adjusted depths and/or x and y coordinates. Processing logic may then create an accurate virtual three dimensional model of the imaged object.

Figure 7:
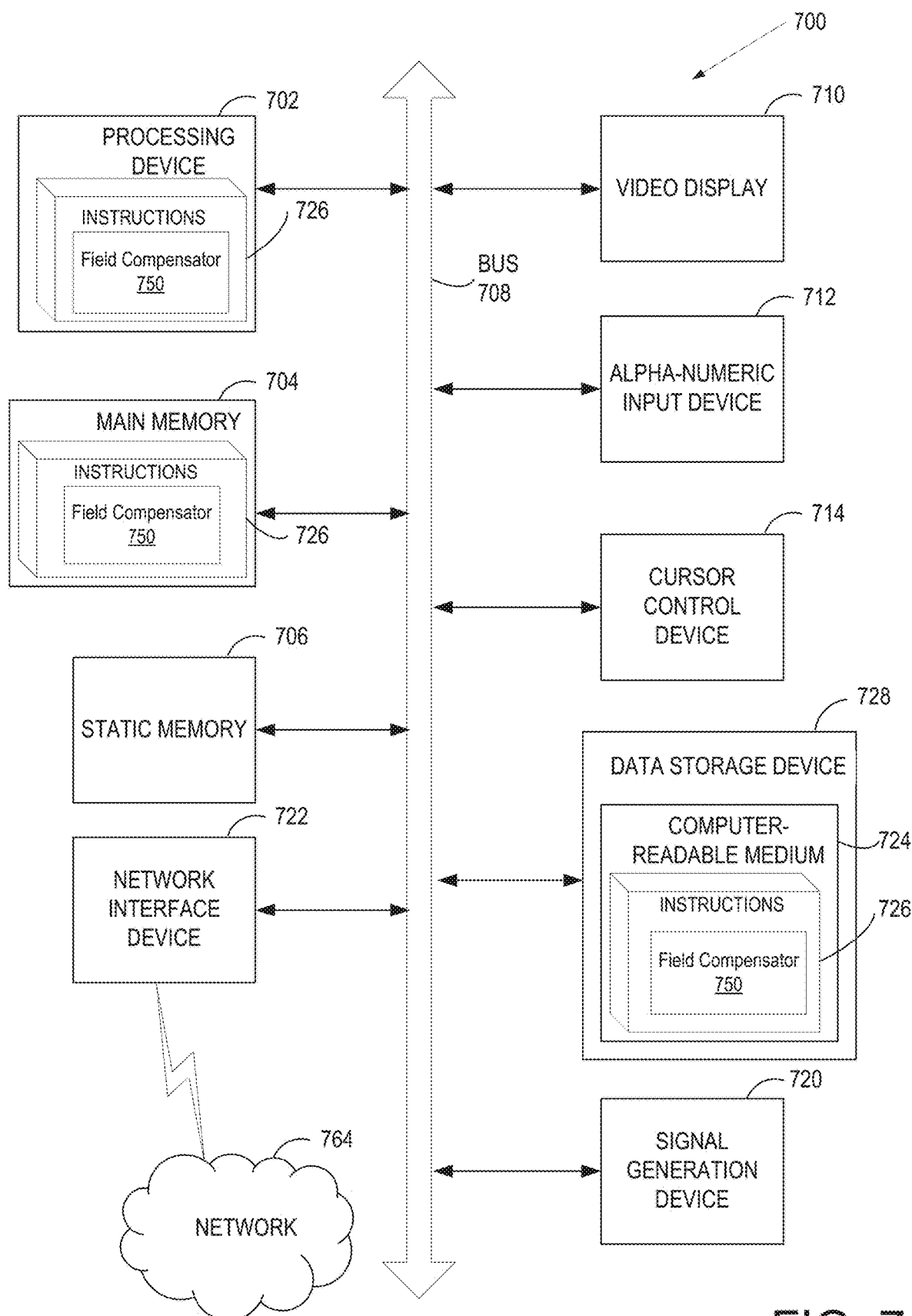
FIG. 7 illustrates a block diagram of an example computing device, in accordance with embodiments of the present invention.

FIG. 7 illustrates a diagrammatic representation of a machine in the example form of a computing device 700 within which a set of instructions, for causing the machine to perform any one or more of the methodologies discussed herein, may be executed. In alternative embodiments, the machine may be connected (e.g., networked) to other machines in a Local Area Network (LAN), an intranet, an extranet, or the Internet. The machine may operate in the capacity of a server or a client machine in a client-server network environment, or as a peer machine in a peer-to-peer (or distributed) network environment. The machine may be a personal computer (PC), a tablet computer, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single machine is illustrated, the term "machine" shall also be taken to include any collection of machines (e.g., computers) that individually or jointly execute a set (or multiple sets) of instructions to perform any one or more of the methodologies discussed herein. In one embodiment, computing device 700 corresponds to computing device 24 of FIG. 1B.

The example computing device 700 includes a processing device 702, a main memory 704 (e.g., read-only memory (ROM), flash memory, dynamic random access memory (DRAM) such as synchronous DRAM (SDRAM), etc.), a static memory 706 (e.g., flash memory, static random access memory (SRAM), etc.), and a secondary memory (e.g., a data storage device 728), which communicate with each other via a bus 708.

Processing device 702 represents one or more general-purpose processors such as a microprocessor, central processing unit, or the like. More particularly, the processing device 702 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processing device 702 may also be one or more special-purpose processing devices such as an application specific integrated circuit (ASIC), a field programmable gate array (FPGA), a digital signal processor (DSP), network processor, or the like. Processing device 702 is configured to execute the processing logic (instructions 726) for performing operations and steps discussed herein.

The computing device 700 may further include a network interface device 722 for communicating with a network 764 or other device. The computing device 700 also may include a video display unit 710 (e.g., a liquid crystal display (LCD) or a cathode ray tube (CRT)), an alphanumeric input device 712 (e.g., a keyboard), a cursor control device 714 (e.g., a mouse), and a signal generation device 720 (e.g., a speaker).

The data storage device 728 may include a machine-readable storage medium (or more specifically a non-transitory computer-readable storage medium) 724 on which is stored one or more sets of instructions 726 embodying any one or more of the methodologies or functions described herein. A non-transitory storage medium refers to a storage medium other than a carrier wave. The instructions 726 may also reside, completely or at least partially, within the main memory 704 and/or within the processing device 702 during execution thereof by the computer device 700, the main memory 704 and the processing device 702 also constituting computer-readable storage media.

The computer-readable storage medium 724 may also be used to store a field compensator 750 which may correspond to field compensator 92 of FIG. 1B. The computer readable storage medium 724 may also store a software library containing methods that call the field compensator 750. While the computer-readable storage medium 724 is shown in an example embodiment to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium that is capable of storing or encoding a set of instructions for execution by the machine and that cause the machine to perform any one or more of the methodologies of the present invention. The term "computer-readable storage medium" shall accordingly be taken to include, but not be limited to, solid-state memories, and optical and magnetic media.

It is to be understood that the above description is intended to be illustrative, and not restrictive. Many other embodiments will be apparent upon reading and understanding the above description. Although embodiments of the present invention have been described with reference to specific example embodiments, it will be recognized that the invention is not limited to the embodiments described, but can be practiced with modification and alteration within the spirit and scope of the appended claims. Accordingly, the specification and drawings are to be regarded in an illustrative sense rather than a restrictive sense. The scope of the invention should, therefore, be determined with reference to the appended claims, along with the full scope of equivalents to which such claims are entitled.

What is claimed is:

1. An imaging apparatus for performing intraoral scans, comprising:
    a light source to provide light;
    an optical system comprising a plurality of lenses disposed along an optical path of the light, wherein the optical system comprises a non-flat focal surface, and wherein the optical system comprises focusing optics to perform focusing of the light onto the non-flat focal surface and to direct the light toward a three dimensional object to be imaged in an oral cavity;

a translation mechanism to adjust a location of at least one lens of the plurality of lenses to thereby adjust a focusing setting of the optical system and displace the non-flat focal surface along an imaging axis defined by the optical path, wherein the at least one lens is a lens of the focusing optics, and wherein at least one of a shape or a magnification of the non-flat focal surface changes with changes in the focusing setting; and a detector to measure intensities of returning light that is reflected off of the three dimensional object and directed back through the focusing optics, wherein the intensities of the returning light are to be measured for a plurality of locations of the at least one lens for determination of positions on the imaging axis of a plurality of points of the three dimensional object, wherein detected positions of one or more of the plurality of points are to be adjusted to compensate for the non-flat focal surface using one or more compensation models that provide different adjustments for different focusing settings of the optical system.

2. The imaging apparatus of claim 1, wherein the non-flat focal surface comprises a curved focal plane and the detected positions for the one or more of the plurality of points are to be adjusted to compensate for a curvature of the curved focal plane.

3. The imaging apparatus of claim 1, further comprising:
a beam splitter disposed along the optical path between the light source and the focusing optics, wherein the beam splitter directs the light from the light source towards the focusing optics and directs the returning light from the focusing optics to the detector;
wherein the imaging apparatus is characterized in having an absence of a field lens between the beam splitter and the light source.

4. The imaging apparatus of claim 3, wherein the imaging apparatus is further characterized in having an absence of a field lens between the beam splitter and the detector.

5. The imaging apparatus of claim 3, wherein the light source comprises an illumination module configured to generate an array of light in an x-y plane.

6. The imaging apparatus of claim 1, further comprising:
a folding prism along the optical path of the light after the focusing optics, wherein the folding prism is to direct the light onto the three dimensional object to be imaged;
wherein the plurality of lenses comprise:
a first lens group;
a second lens group disposed proximate to the folding prism, the second lens group having a fixed location relative to the first lens group; and
a third lens group disposed between the first lens group and the second lens group, the third lens group having a variable location that is adjustable by the translation mechanism, wherein the focusing optics comprises the third lens group.

7. The imaging apparatus of claim 1, wherein a radius of a largest lens of the plurality of lenses is less than 13 millimeters.

8. The imaging apparatus of claim 1, wherein the imaging apparatus is a confocal imaging apparatus, and wherein the optical system is a confocal optical system, the imaging apparatus further comprising a processor to:

determine a location of the at least one lens that yields a maximum measured intensity for a portion of the returning light;
determine a position on the imaging axis of a point of the three dimensional object illuminated by the portion of the returning light that corresponds to the determined location of the at least one lens; and
adjust the position on the imaging axis of the point of the three dimensional object based on applying the determined location of the at least one lens to a field curvature model that is calibrated to the imaging apparatus to compensate for the non-flat focal surface.

9. The imaging apparatus of claim 1, wherein the optical system is a non-telecentric optical system.

10. The imaging apparatus of claim 8, further comprising:
one or more elements near or along the optical path, the one or more elements having a fixed distance from a first lens of the plurality of lenses, wherein the fixed distance changes with changes in temperature, wherein the processor is further to:
determine a current distance between the one or more elements and the first lens; and
apply an adjustment factor to the field curvature model based on the current distance.

11. An imaging apparatus for performing intraoral scans, comprising:
a light source to provide light comprising a plurality of light beams;
optics comprising a plurality of lenses disposed along an optical path of the light, wherein the optics comprises focusing optics to perform focusing of the light onto a focal surface and to direct the light toward a three dimensional object to be imaged in an oral cavity, and wherein the optics are characterized by an absence of a field lens, wherein the field lens is a diverging lens that opens rays of the plurality of light beams;
a translation mechanism to adjust a location of at least one lens of the plurality of lenses to displace the focal surface along an imaging axis defined by the optical path, wherein the at least one lens is a lens of the focusing optics; and
a detector to measure intensities of returning light that is reflected off of the three dimensional object and directed back through the focusing optics, wherein the intensities of the returning light are to be measured for a plurality of locations of the at least one lens for determination of positions on the imaging axis of a plurality of points of the three dimensional object, wherein detected positions of one or more of the plurality of points are to be adjusted to compensate for the absence of the field lens.

12. The imaging apparatus of claim 11, wherein the absence of the field lens causes the focusing optics to perform the focusing of the light onto a non-flat focal surface.

13. The imaging apparatus of claim 12, wherein the non-flat focal surface comprises a curved focal plane, wherein the detected positions for the one or more of the plurality of points are to be adjusted to compensate for a curvature of the curved focal plane, and wherein a shape of the non-flat focal surface changes with changes in the location of the at least one lens.

14. The imaging apparatus of claim 11, further comprising:
a beam splitter disposed along the optical path between the light source and the focusing optics, wherein the beam splitter directs the light from the light source towards the focusing optics and directs the returning light from the focusing optics to the detector.

15. The imaging apparatus of claim 14, wherein the light source comprises an illumination module configured to generate an array of light in an x-y plane.

16. The imaging apparatus of claim 12, further comprising:
a folding prism along the optical path of the light after the focusing optics, wherein the folding prism is to direct the light onto the three dimensional object to be imaged;
wherein the plurality of lenses comprise:
a first lens group;
a second lens group disposed proximate to the folding prism, the second lens group having a fixed location relative to the first lens group; and
a third lens group disposed between the first lens group and the second lens group, the third lens group having a variable location that is adjustable by the translation mechanism, wherein the focusing optics comprises the third lens group.

17. The imaging apparatus of claim 11, wherein a radius of a largest lens of the plurality of lenses is less than 13 millimeters.

18. The imaging apparatus of claim 11, wherein the imaging apparatus is a confocal imaging apparatus, and wherein the optics are confocal optics, the imaging apparatus further comprising a processor to:
determine locations of the at least one lens that yields yield a maximum measured intensity for portions of the returning light;
determine positions on the imaging axis of points of the three dimensional object illuminated by the portions of the returning light that corresponds correspond to the determined locations of the at least one lens; and
adjust the positions on the imaging axis of the points of the three dimensional object based on applying the determined locations of the at least one lens to one or more field curvature models that are calibrated to the imaging apparatus to compensate for the absence of the field lens, wherein the one or more field curvature models provide different adjustments for different locations of the at least one lens.

19. An imaging apparatus for performing intraoral scans, comprising:
a light source to provide light;
a non-telecentric optical system comprising a plurality of lenses disposed along an optical path of the light, wherein the non-telecentric optical system comprises focusing optics to perform focusing of the light onto a focal surface and to direct the light toward a three dimensional object to be imaged in an oral cavity, the focusing optics comprising at least one lens of the plurality of lenses;
a translation mechanism to adjust a location of the at least one lens to displace the focal surface along an imaging axis defined by the optical path, wherein adjustments to the location of the at least one lens cause a change in magnification of the focal surface; and
a detector to measure intensities of returning light that is reflected off of the three dimensional object and directed back through the focusing optics, wherein the intensities of the returning light are to be measured for a plurality of locations of the at least one lens for determination of positions on the imaging axis of a plurality of points of the three dimensional object, wherein detected positions of one or more of the plurality of points are to be adjusted to compensate for respective magnifications of the focal surface associated with respective locations of the plurality of locations of the at least one lens.

20. The imaging apparatus of claim 19, wherein the focusing optics perform the focusing of the light onto a non-flat focal surface.

21. The imaging apparatus of claim 20, wherein the non-flat focal surface comprises a curved focal plane, wherein the detected positions for the one or more of the plurality of points are to be adjusted to compensate for a curvature of the curved focal plane, and wherein a shape of the non-flat focal surface changes with changes in the location of the at least one lens.

22. The imaging apparatus of claim 19, further comprising:
a beam splitter disposed along the optical path between the light source and the focusing optics, wherein the beam splitter directs the light from the light source towards the focusing optics and directs the returning light from the focusing optics to the detector;
wherein the imaging apparatus is characterized in having an absence of a field lens between the beam splitter and the light source, and is further characterized in having an absence of a field lens between the beam splitter and the detector.

23. The imaging apparatus of claim 22, wherein the light source comprises an illumination module configured to generate an array of light beams in an x-y plane, wherein the imaging apparatus is a confocal imaging apparatus, and wherein the non-telecentric optical system is a confocal optical system.

24. The imaging apparatus of claim 19, wherein the light source comprises a semiconductor laser unit.

25. The imaging apparatus of claim 19, further comprising:
a folding prism along the optical path of the light after the focusing optics, wherein the folding prism is to direct the light onto the three dimensional object to be imaged;
wherein the plurality of lenses comprise:
a first lens group;
a second lens group disposed proximate to the folding prism, the second lens group having a fixed location relative to the first lens group; and
a third lens group disposed between the first lens group and the second lens group, the third lens group having a variable location that is adjustable by the translation mechanism, wherein the focusing optics comprises the third lens group.

26. The imaging apparatus of claim 19, wherein a radius of a largest lens of the plurality of lenses is less than 13 millimeters.

27. A method of performing an intraoral scan, comprising:
providing light;
directing, via an optical system comprising a non-flat focal surface, the light toward a three dimensional object to be imaged in an oral cavity;
performing focusing of the light onto the non-flat focal surface using focusing optics comprising a plurality of lenses disposed along an optical path of the light;
adjusting a location of at least one lens of the plurality of lenses to displace the non-flat focal surface along an imaging axis defined by the optical path using a translation mechanism;
measuring intensities of returning light that is reflected off of the three dimensional object and directed back through the focusing optics, wherein the intensities of the returning light are measured for a plurality of locations of the at least one lens for determination of positions on the imaging axis of a plurality of points of the three dimensional object; and adjusting detected positions of one or more of the plurality of points to compensate for the non-flat focal surface using one or more compensation models that provide different adjustments for different focusing settings of the focusing optics.

28. The method of claim 27, wherein the focusing comprises confocal focusing, the method further comprising:

determining a location of the at least one lens that yields a maximum measured intensity for a portion of the returning light;

determining a position on the imaging axis of a point of the three dimensional object illuminated by the portion of the returning light that corresponds to the determined location of the at least one lens; and adjusting the position on the imaging axis of the point of the three dimensional object based on applying the determined location of the at least one lens to a field curvature model that is calibrated to compensate for the non-flat focal surface.

29. The method of claim 28, wherein the field curvature model comprises a three dimensional polynomial function.

30. The method of claim 27, wherein the non-flat focal surface comprises a curved focal plane and the detected positions for the one or more of the plurality of points are adjusted to compensate for a curvature of the curved focal plane.

* * * * *